US009844366B2

United States Patent
Woodard, Jr. et al.

(10) Patent No.: US 9,844,366 B2
(45) Date of Patent: Dec. 19, 2017

(54) NEEDLE FOR LAPAROSCOPIC SUTURING INSTRUMENT

(71) Applicant: Ethicon Endo-Surgery, Inc., Cincinnati, OH (US)

(72) Inventors: James A. Woodard, Jr., Apex, NC (US); Michael V. Sherrill, Batavia, OH (US); Jason R. Lesko, Harrison, OH (US); David T. Martin, Milford, OH (US); Katherine J. Schmid, Loveland, OH (US); Michael J. Miller, Mason, OH (US); Gary W. Knight, West Chester, OH (US); Richard F. Schwemberger, Cincinnati, OH (US); Atul M. Godbole, Liberty Township, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 185 days.

(21) Appl. No.: 14/814,841

(22) Filed: Jul. 31, 2015

(65) Prior Publication Data

US 2016/0015383 A1  Jan. 21, 2016

Related U.S. Application Data

(62) Division of application No. 13/295,186, filed on Nov. 14, 2011, now Pat. No. 9,125,646.

(Continued)

(51) Int. Cl.
*A61B 17/06* (2006.01)
*A61B 17/04* (2006.01)
(Continued)

(52) U.S. Cl.
CPC .. *A61B 17/06004* (2013.01); *A61B 17/06066* (2013.01); *A61B 17/0469* (2013.01);
(Continued)

(58) Field of Classification Search
CPC ........ A61B 17/06066; A61B 17/06004; A61B 2017/06019; A61B 2017/06052;
(Continued)

(56) References Cited

U.S. PATENT DOCUMENTS 4,527,564 A   7/1985  Eguchi et al.
5,030,228 A * 7/1991  Wong ............... A61B 17/06066
                                              606/222

(Continued)

FOREIGN PATENT DOCUMENTS

EP  0 687 446 A2  12/1995
EP  0 985 382 A1   3/2000
(Continued)

OTHER PUBLICATIONS

International Search Report dated Feb. 2, 2012 for Application No. PCT/US2011/060575, 7 pgs.

(Continued)

*Primary Examiner* — Richard Louis
(74) *Attorney, Agent, or Firm* — Frost Brown Todd LLC

(57) ABSTRACT

A surgical needle includes a pair of ends, a mid-region extending between the ends, and at least one grasping feature configured for grasping by a suturing instrument. An end of a suture is secured to the mid-region of the needle in a manner such that the end of the suture defines an oblique angle with at least part of the centerline defined by the mid-region of the needle. The end of the suture may be disposed in a hollow portion of the needle. The grasping feature may include a notch such as a scallop. The suture may be pivotally coupled with the needle via a ball or pin.

(Continued)

The needle may have one or more sharp points. The sharp point may include three converging cutting edges, at least two planar surfaces bounded by the three cutting edges, and a rounded surface bounded by two of the three cutting edges.

19 Claims, 24 Drawing Sheets

Related U.S. Application Data

(60) Provisional application No. 61/413,680, filed on Nov. 15, 2010.

(51) Int. Cl.
*A61B 17/062* (2006.01)
*A61B 17/29* (2006.01)

(52) U.S. Cl.
CPC ....... *A61B 17/062* (2013.01); *A61B 2017/061* (2013.01); *A61B 2017/06009* (2013.01); *A61B 2017/0609* (2013.01); *A61B 2017/06019* (2013.01); *A61B 2017/06023* (2013.01); *A61B 2017/06047* (2013.01); *A61B 2017/06052* (2013.01); *A61B 2017/2929* (2013.01)

(58) Field of Classification Search
CPC .. A61B 2017/06047; A61B 2017/2929; A61B 2017/061; A61B 2017/06009; A61B 17/062; A61B 17/0469; A61B 2017/0609
See application file for complete search history.

(56) References Cited

U.S. PATENT DOCUMENTS

| | | | |
|---|---|---|---|
| 5,792,180 | A | 8/1998 | Munoz |
| 5,941,899 | A * | 8/1999 | Granger ........... A61B 17/06066 163/5 |
| 6,056,771 | A | 5/2000 | Proto |
| 6,071,289 | A | 6/2000 | Stefanchik et al. |
| 6,129,741 | A | 10/2000 | Wurster et al. |
| 6,322,581 | B1 * | 11/2001 | Fukuda ............ A61B 17/06066 606/222 |
| 7,628,796 | B2 | 12/2009 | Shelton, IV et al. |
| 8,702,732 | B2 | 4/2014 | Woodard, Jr. et al. |
| 9,011,487 | B2 | 4/2015 | Lindh et al. |
| 9,125,646 | B2 | 9/2015 | Woodard et al. |
| 9,168,037 | B2 | 10/2015 | Woodard, Jr. et al. |
| 2008/0161850 | A1 | 7/2008 | Weisenburgh et al. |
| 2010/0100125 | A1 * | 4/2010 | Mahadevan ..... A61B 17/06066 606/223 |

FOREIGN PATENT DOCUMENTS

| | | |
|---|---|---|
| EP | 1 201 189 A2 | 5/2002 |
| WO | 97/37594 A1 | 10/1997 |

OTHER PUBLICATIONS

International Preliminary Report on Patentability and Written Opinion dated May 21, 2013 for Application No. PCT/US2011/060575, 12 pgs.
U.S. Appl. No. 61/355,832, filed Jun. 17, 2010.

* cited by examiner

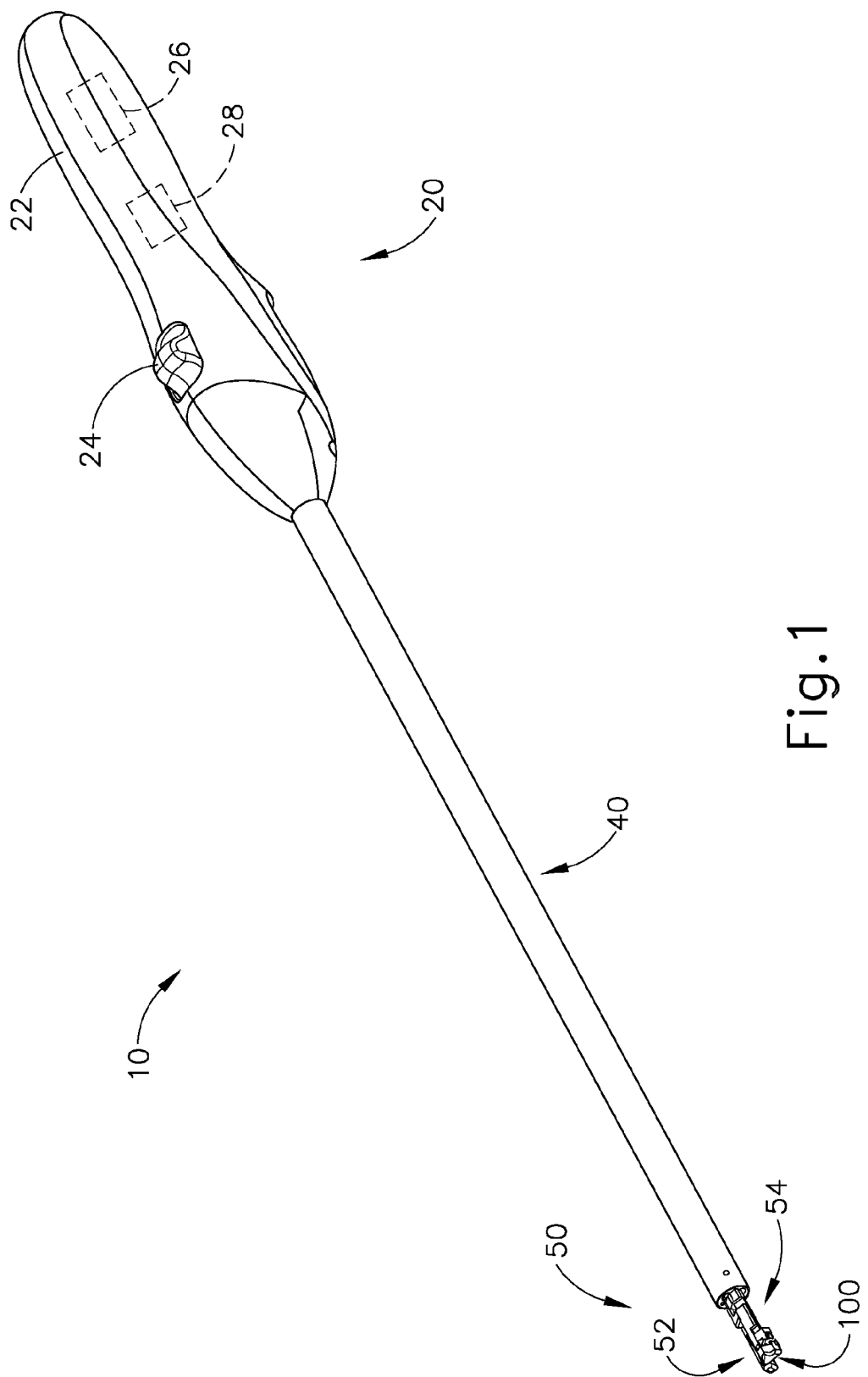

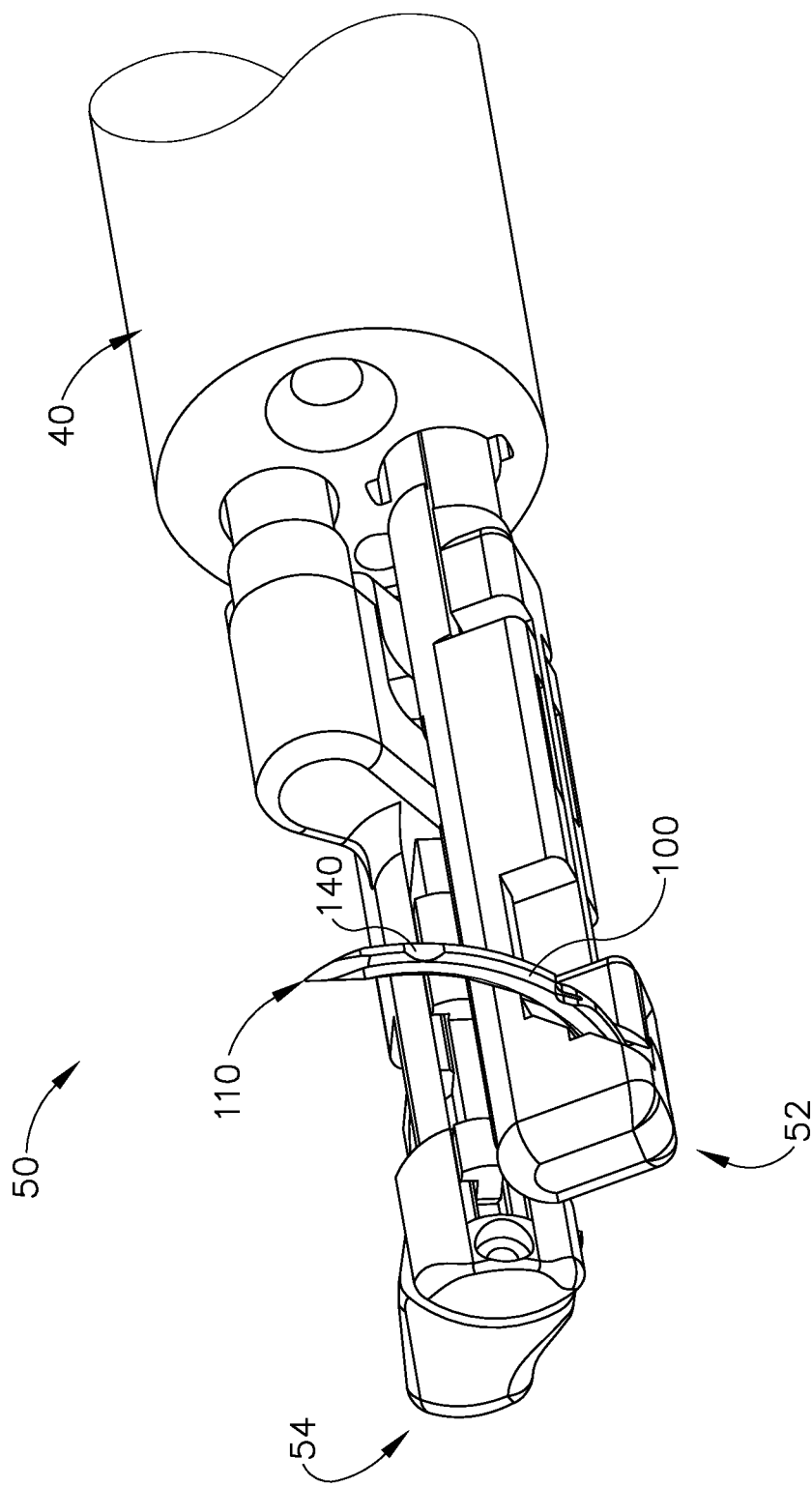

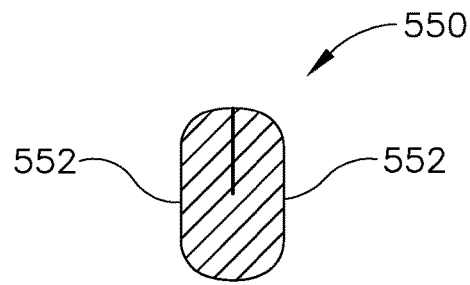
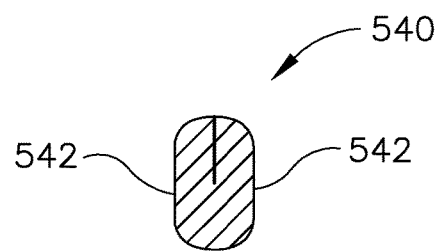
Fig.14          Fig.16
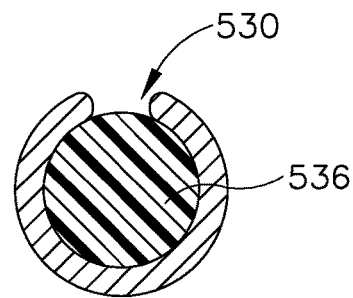
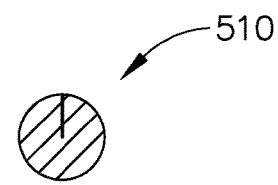
Fig.15          Fig.17

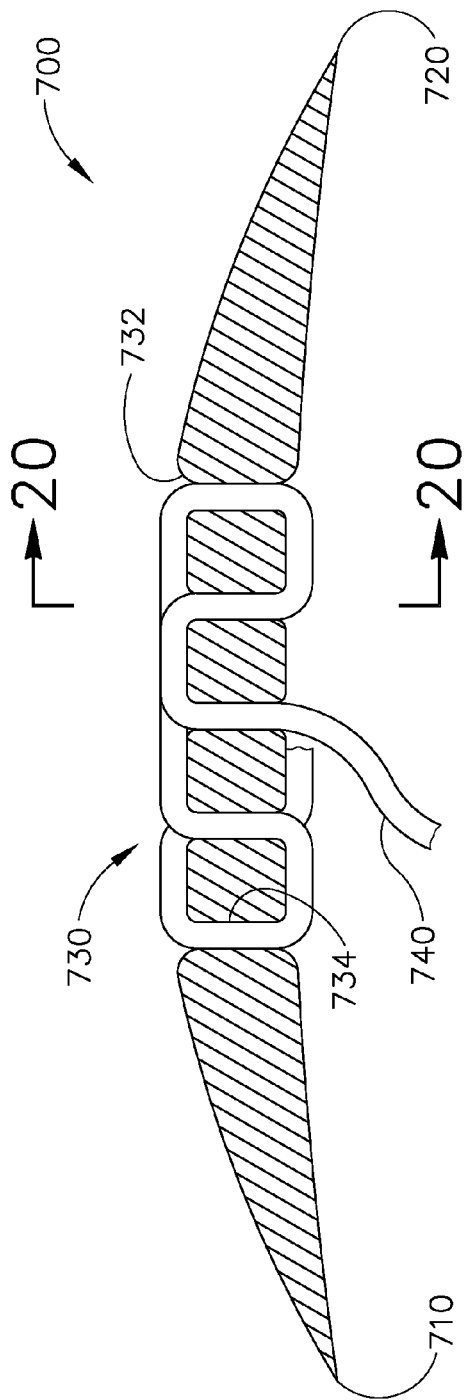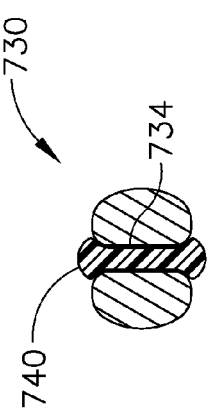
Fig.19
Fig.20

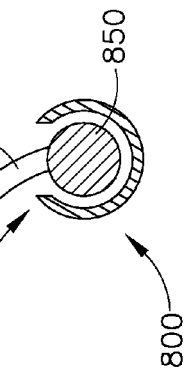
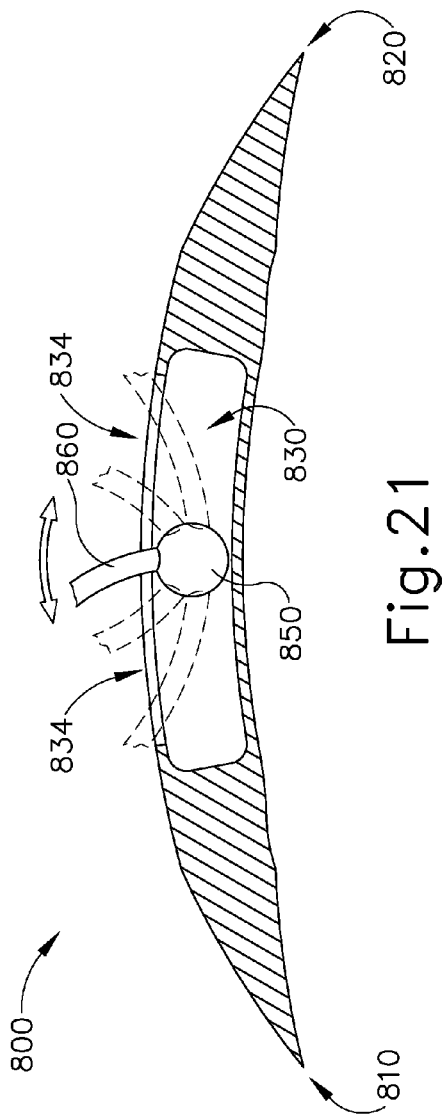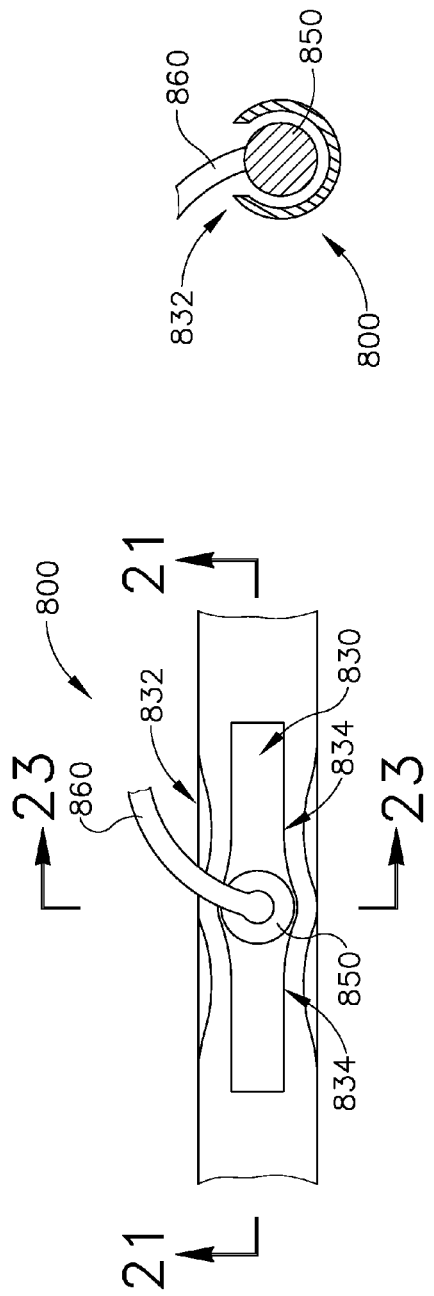

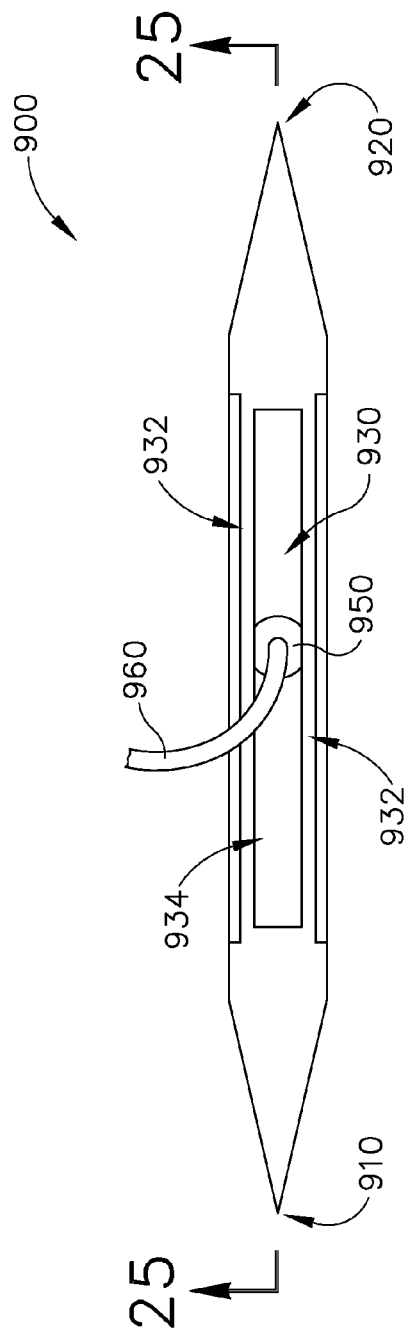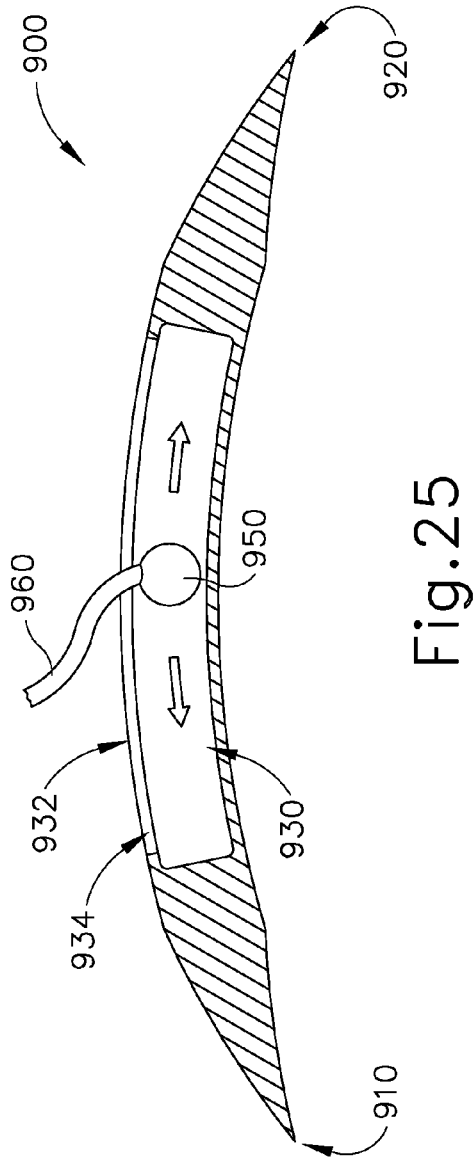

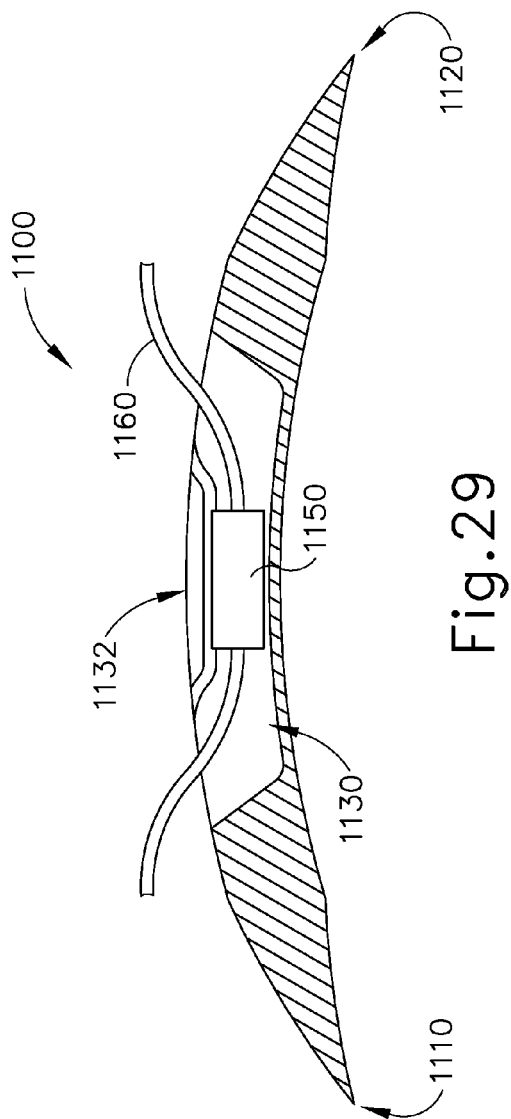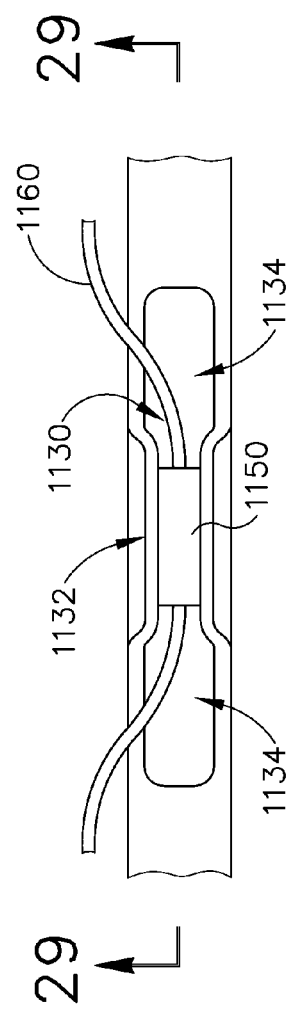

NEEDLE FOR LAPAROSCOPIC SUTURING INSTRUMENT

PRIORITY

This application is a division of U.S. patent application Ser. No. 13/295,186, filed Nov. 14, 2011, entitled "Needle For Laparoscopic Suturing Instrument," now U.S. Pat. No. 9,125,646, issued on Sep. 8, 2015, which claims priority to U.S. Provisional Application Ser. No. 61/413,680, filed Nov. 15, 2010, entitled "Custom Needle for Suture Instrument," the disclosure of which is incorporated by reference herein.

BACKGROUND

In some settings it may be desirable to perform a surgical procedure in a minimally invasive manner, such as through a trocar or other type of access cannula. Examples of trocars include the various ENDOPATH® EXCEL™ products by Ethicon Endo-Surgery, Inc. of Cincinnati, Ohio. Such trocars may present different inner diameters, such as those ranging from approximately 4.7 mm to approximately 12.9 mm, allowing a surgeon to choose a particular trocar based on a balance of considerations such as access needs and incision size. In some minimally invasive surgical procedures, at least two trocars may be inserted through the abdominal wall of the patient. An imaging device such as an endoscope may be inserted through one of the trocars to provide visualization of the surgical site. A surgical instrument may be inserted through another one of the trocars to perform surgery at the site. In procedures performed within the abdominal cavity, the cavity may be insufflated with pressurized carbon dioxide to provide more room for visualization and manipulation of instruments. In some settings, additional trocars may be used to provide access for additional surgical instruments. Minimally invasive surgery may also be performed through access portals such as the Single Site Laparoscopy Access System by Ethicon Endo-Surgery, Inc. of Cincinnati, Ohio, which provides ports for more than one surgical instrument through a single incision in a patient.

It may also be desirable to use sutures during some minimally invasive surgical procedures, such as to close an opening, to secure two layers of tissue together, to provide an anastomosis, etc. Such use of sutures may be in addition to or in lieu of using other devices and techniques such as clips, staples, electrosurgical sealing, etc. Performing suturing through trocars or other minimally invasive access ports may be more difficult than suturing in an open surgical procedure. For instance, manipulating a needle and suture with conventional tissue graspers through trocars may be relatively difficult for many surgeons. Thus, improved laparascopic surgical instruments may make suturing procedures performed through trocars relatively easier. Examples of surgical instruments configured to facilitate suturing through trocars include the LAPRA-TY® Suture Clip Applier, the Suture Assistant, and the ENDOPATH® Needle Holder, all of which are by Ethicon Endo-Surgery, Inc. of Cincinnati, Ohio. Additional suturing instruments are disclosed in U.S. Pat. No. 7,628,796, entitled "Surgical Suturing Apparatus with Anti-Backup System," issued Dec. 8, 2009, the disclosure of which is incorporated by reference herein; U.S. Pat. No. 6,071,289, entitled "Surgical Device for Suturing Tissue," issued Jun. 6, 2000, the disclosure of which is incorporated by reference herein; U.S. patent application Ser. No. 13/156,420, entitled "Laparoscopic Suture Device with Asynchronous In-Line Needle Movement," filed Jun. 9, 2011, published as U.S. Pub. No. 2011/0313433 on Dec. 22, 2011, now U.S. Pat. No. 9,168,037, issued on Oct. 27, 2015, the disclosure of which is incorporated by reference herein; U.S. Patent Application No. 13/295,203, entitled "Laparoscopic Suturing Instrument with Dual-Action Needle Graspers," filed Nov. 14, 2011, issued as U.S. Pat. No. 8,702,732 on Apr. 22,2014, the disclosure of which is incorporated by reference herein; and U.S.Provisional Patent Application No. 61/355,832, entitled "Laparoscopic Suture Device," filed Jun. 17, 2010, the disclosure of which is incorporated by reference herein.

Exemplary suturing needles are disclosed in U.S. Pat. No. 6,056,771, entitled "Radiused Tip Surgical Needles and Surgical Incision Members," issued May 2, 2000, the disclosure of which is incorporated by reference herein; and U.S. Pub. No. 2010/0100125, entitled "Suture Needle and Suture Assembly," published Apr. 22, 2010, now abandoned, the disclosure of which is incorporated by reference herein.

While a variety of devices and methods have been made and used for suturing tissue, it is believed that no one prior to the inventor(s) has made or used the technology described herein.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a perspective view of an exemplary laparoscopic suturing instrument;

FIG. 2A depicts a perspective view of the end effector of the suturing instrument of FIG. 1 with the needle of FIG. 4, in a first operational configuration;

FIG. 14 depicts a cross-sectional view of the needle of FIG. 13, taken along line 14-14 of FIG. 13;

FIG. 15 depicts a cross-sectional view of the needle of FIG. 13, taken along line 15-15 of FIG. 13;

FIG. 16 depicts a cross-sectional view of the needle of FIG. 13, taken along line 16-16 of FIG. 13;

FIG. 17 depicts a cross-sectional view of the needle of FIG. 13, taken along line 17-17 of FIG. 13

FIG. 19 depicts a side cross-sectional view of another exemplary alternative suturing needle;

FIG. 20 depicts a cross-sectional view of the needle of FIG. 19, taken along line 20-20 of FIG. 19;

FIG. 21 depicts a side cross-sectional view, taken along line 21-21 of FIG. 22, of another exemplary alternative suturing needle;

FIG. 22 depicts a partial top plan view of the needle of FIG. 21;

FIG. 23 depicts a cross-sectional view of the needle of FIG. 21, taken along line 23-23 of FIG. 22;

FIG. 24 depicts a top plan view of another exemplary alternative suturing needle;

FIG. 25 depicts a side cross-sectional view of the needle of FIG. 24, taken along line 25-25 of FIG. 24;

FIG. 29 depicts a side cross-sectional view, taken along line 29-29 of FIG. 30, of another exemplary alternative suturing needle;

FIG. 30 depicts a partial top plan view of the needle of FIG. 29;

Figure 2B:
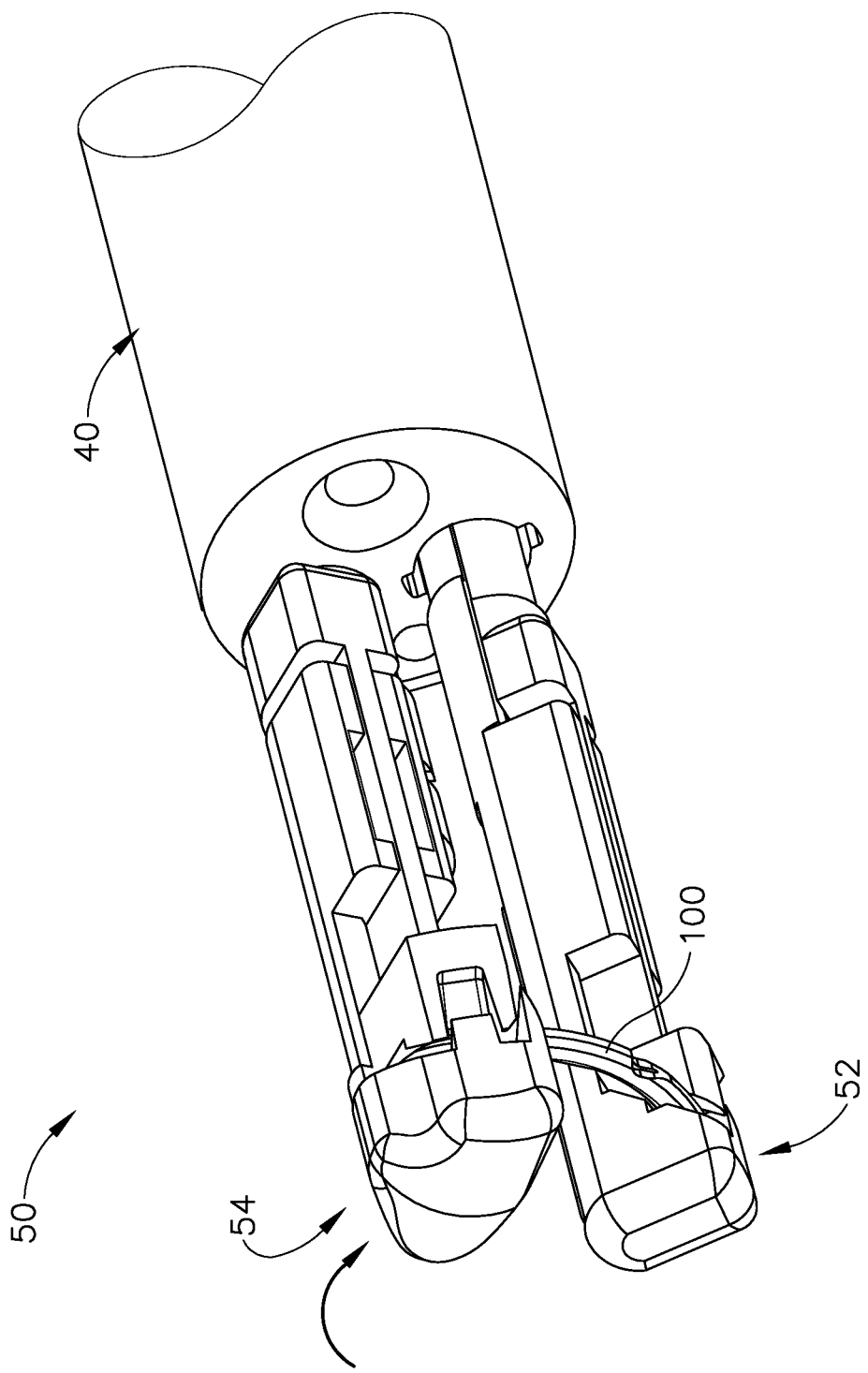
FIG. 2B depicts a perspective view of the end effector and needle of FIG. 2A, in a second operational configuration.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It should therefore be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview

FIG. 1 shows an exemplary laparoscopic suturing instrument (10). Instrument (10) of this example includes a handle portion (20), a shaft (40) extending distally from handle portion (20), and an end effector (50) at the distal end of shaft (40). Handle portion (20) includes a grip (22), a rocker (24), an integral power source (26), and a motor (28) in communication with the integral power source (26). Rocker (24) is resiliently biased to a generally vertical position (e.g., generally perpendicular to grip (22)), though rocker (24) may be rocked forwardly or rearwardly. In addition or in the alternative, rocker (24) may be rocked to the left or to the right. Rocker (24) is operable to actuate features of end effector (50) as will be described in greater detail below. Of course, rocker (24) is merely one example of a user input feature, and any other suitable type of user input feature may be used.

Integral power source (26) comprises a rechargeable battery in the present example, though it should be understood that any other suitable power source may be used. By way of example only, instrument (10) may use a power source that is external to instrument (10) (e.g., coupled with instrument (10) via a cable, etc.). Similarly, while end effector (50) is powered by motor (28) in the present example, it should be understood that any other suitable source may be used, including but not limited to a manually operable mechanism. One merely illustrative example of a manually operable instrument is described below with reference to FIG. 3. Various other suitable components, features, and configurations for handle portion (20) will be apparent to those of ordinary skill in the art in view of the teachings herein. By way of example only, handle portion (20) may be constructed in accordance with at least some of the teachings of U.S. Provisional Patent Application No. 61/355,832, the disclosure of which is incorporated by reference herein; in accordance with at least some of the teachings of U.S. patent application Ser. No. 13/156,420, published as U.S. Pub. No. 2011/0313433 on Dec. 22, 2011, now U.S. Pat. No. 9,168,037, issued on Oct. 27, 2015, the disclosure of which is incorporated by reference herein; and/or in accordance with the teachings of U.S. patent application Ser. No. 13/295,203, issued as U.S. Pat. No. 8,702,732 on Apr. 22, 2014, the disclosure of which is incorporated by reference herein.

Shaft (40) of the present example has an outer diameter sized to permit shaft (40) to be inserted through a conventional trocar (not shown). Shaft (40) also has a length sized to permit end effector (50) to be positioned at a surgical site within a patient while also allowing handle portion (20) to be manipulated by a user (e.g., a surgeon) from a location outside the patient when shaft (40) is disposed in a trocar. Of course, shaft (40) need not necessarily be dimensioned for use through a trocar. For instance, instrument (10) may be used and/or configured for use in open surgical procedures.

In some versions, shaft (40) includes one or more articulating features, allowing end effector (50) to be articulated to various angles and positions relative to the longitudinal axis defined by shaft (40). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft (40) may be rotatable about the longitudinal axis, relative to handle portion (20), to selectively position end effector (50) at various angular orientations about the longitudinal axis. Of course, a user may rotate the entire instrument (10) about the longitudinal axis to selectively position end effector (50) at various angular orientations about the longitudinal axis.

End effector (50) of the present example includes a first grasping arm (52) and a second grasping arm (54). As will be described in greater detail below, arms (52, 54) are configured to alternatingly throw and catch a curved suturing needle (100) along a path/plane that is substantially perpendicular to the longitudinal axis defined by shaft (40). Alternatively, arms (52, 54) may be configured to alternatingly throw and catch needle (100) along a path that is substantially parallel to the longitudinal axis defined by shaft (40), as described below with reference to FIG. 3 or otherwise; or along some other path.

In some versions, arms (52, 54) pass needle (100) back and forth from arm (52) to arm (54) and from arm (54) to arm (52) in an oscillating motion (i.e., back and forth in opposite directions), such that needle (100) does not traverse a circular path as needle (100) is being passed between arms (52, 54). Such action of needle (100) may be referred to as a "reverse reset." In some other versions, needle (100) may be passed between arms (52, 54) along a circular path in a single direction. Such action of needle (100) may be referred to as a "forward reset." By way of example only, arms (52, 54) may move in accordance with at least some of the teachings of U.S. Provisional Patent Application No. 61/355,832, the disclosure of which is incorporated by reference herein; in accordance with at least some of the teachings of U.S. patent application Ser. No. 13/156,420, published a U.S. Pub. No. 2011/0313433 on Dec. 22, 2011, now U.S. Pat. No. 9,168,037, issued on Oct. 27, 2015, the disclosure of which is incorporated by reference herein; and/or in accordance with the teachings of U.S. patent application Ser. No. 13/295,203, issued as U.S. Pat. No. 8,702,732 on Apr. 22, 2014 the disclosure of which is incorporated by reference herein. Regardless of whether arms (52, 54) move synchronously or asynchronously, arms (52, 54) may be configured to grip and/or compress tissue that is positioned between arms (52, 54) when arms are in approximated positions, which may facilitate passage of needle (100) through the tissue.

As noted above, grasping arms (52, 54) are operable to selectively grasp needle (100) during a suturing procedure. Each grasping arm (210, 250) extends along a respective axis that is parallel to yet offset from the center axis of shaft (40). First grasping arm (52) maintains a fixed rotational position relative to shaft (40) during operation of instrument (10) in the present example. In some other versions, first grasping arm (52) is rotatable about its own longitudinal axis, relative to shaft (40). Second grasping arm (54) of the present example is rotatable about its longitudinal axis. Such motion can be seen in the series shown by FIGS. 2A-2C.

Figure 2C:
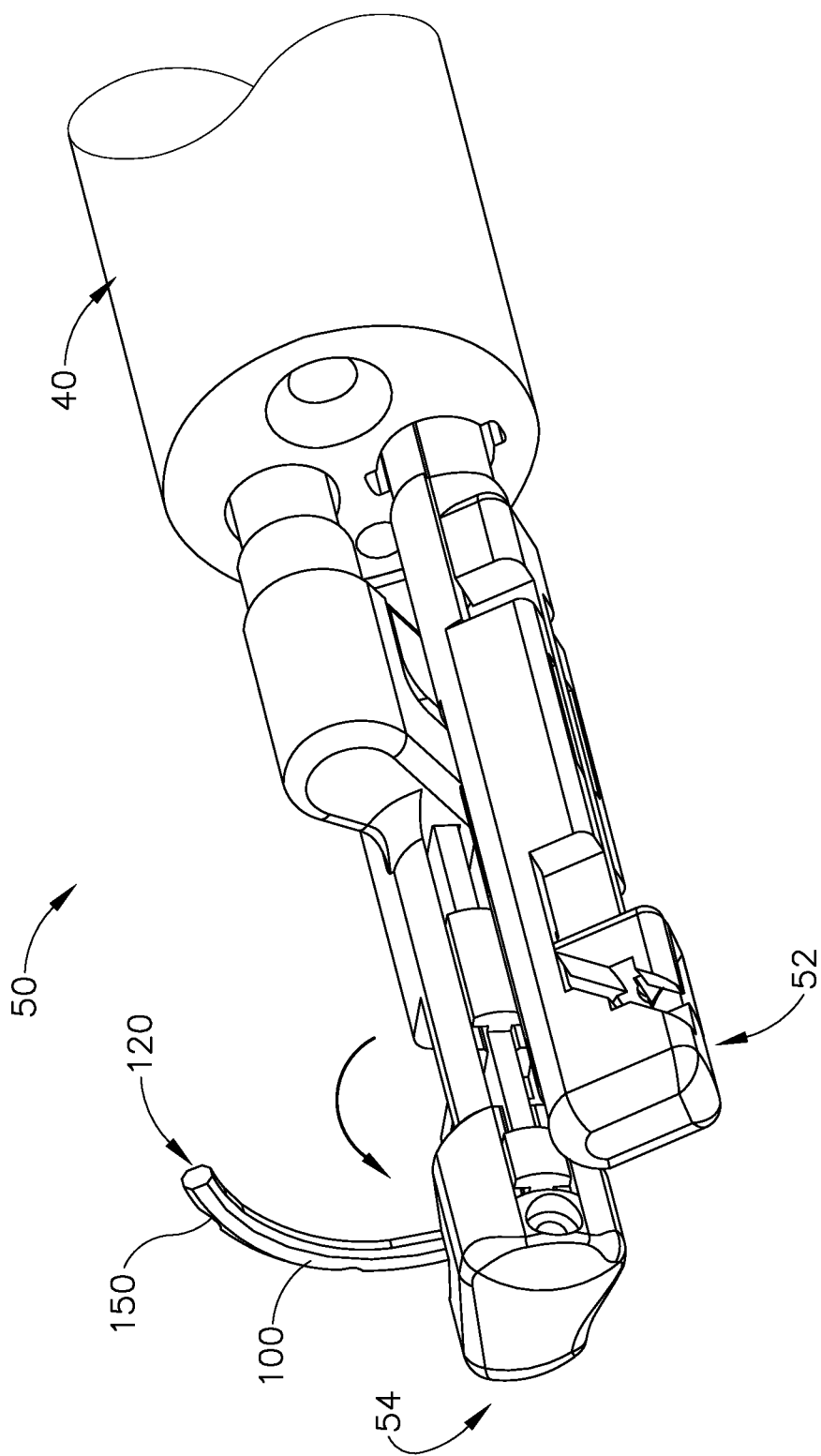
FIG. 2C depicts a perspective view of the end effector and needle of FIG. 2 A, in a third operational configuration.

FIG. 2A shows first grasping arm (52) grasping needle (100), with second grasping arm (54) rotated away from needle (100), exposing sharp tip (110) of needle (100). FIG. 2B shows second grasping arm (54) rotated toward needle (100) to a position enabling second grasping arm (54) to grasp needle (100) and first grasping arm (52) to release needle (100). FIG. 2C shows second grasping arm (54) rotated away from first grasping arm (52), pulling needle (100) away from second grasping arm (54). After reaching this position, second grasping arm (54) may be rotated back to the position shown in FIG. 2B, to thereby pass needle (100) back to first grasping arm (52); then rotate back to the position shown in FIG. 2A to start the cycle over again.

In the examples described herein, needle (100) is driven along a plane that is substantially perpendicular to the longitudinal axis of shaft (40). In some other examples, needle (100) is driven along a plane that is oblique relative to the longitudinal axis of shaft (40) or substantially parallel to the longitudinal axis of shaft (40). During some uses of instrument (10), needle (100) may deviate from the desired perpendicular plane. Such deviation may be due to manufacturing tolerances, deflections caused by tissue or other structures, and/or for other reasons. Such deviation may be accentuated by using a needle (100) having a relatively great length. In some versions, end effector (50) is configured to readily accommodate and correct such off-plane deviations. In other words, arms (52, 54) are operable to grasp needle (100) even in instances where needle (100) has deviated away from the expected perpendicular plane of motion; and arms (52, 54) are further operable to redirect a deviated needle (100) back onto the expected perpendicular plane of motion.

It should be noted that a suture is omitted from FIGS. 2A-2C for clarity. Various exemplary components of grasping arms (52, 54) are described in U.S. patent application Ser. No. 13/295,203, issued as U.S. Pat. No. 8,702,732 on Apr. 22, 2014, the disclosure of which is incorporated by reference herein. Various ways in which grasping arms (52, 54) may be used are also described in U.S. patent application Ser. No. 13/295,203, issued as U.S. Pat. No. 8,702,732 on Apr. 22, 2014 the disclosure of which is incorporated by reference herein. Other suitable components of and uses for grasping arms (52, 54) will be apparent to those of ordinary skill in the art in view of the teachings herein.

Figure 3:
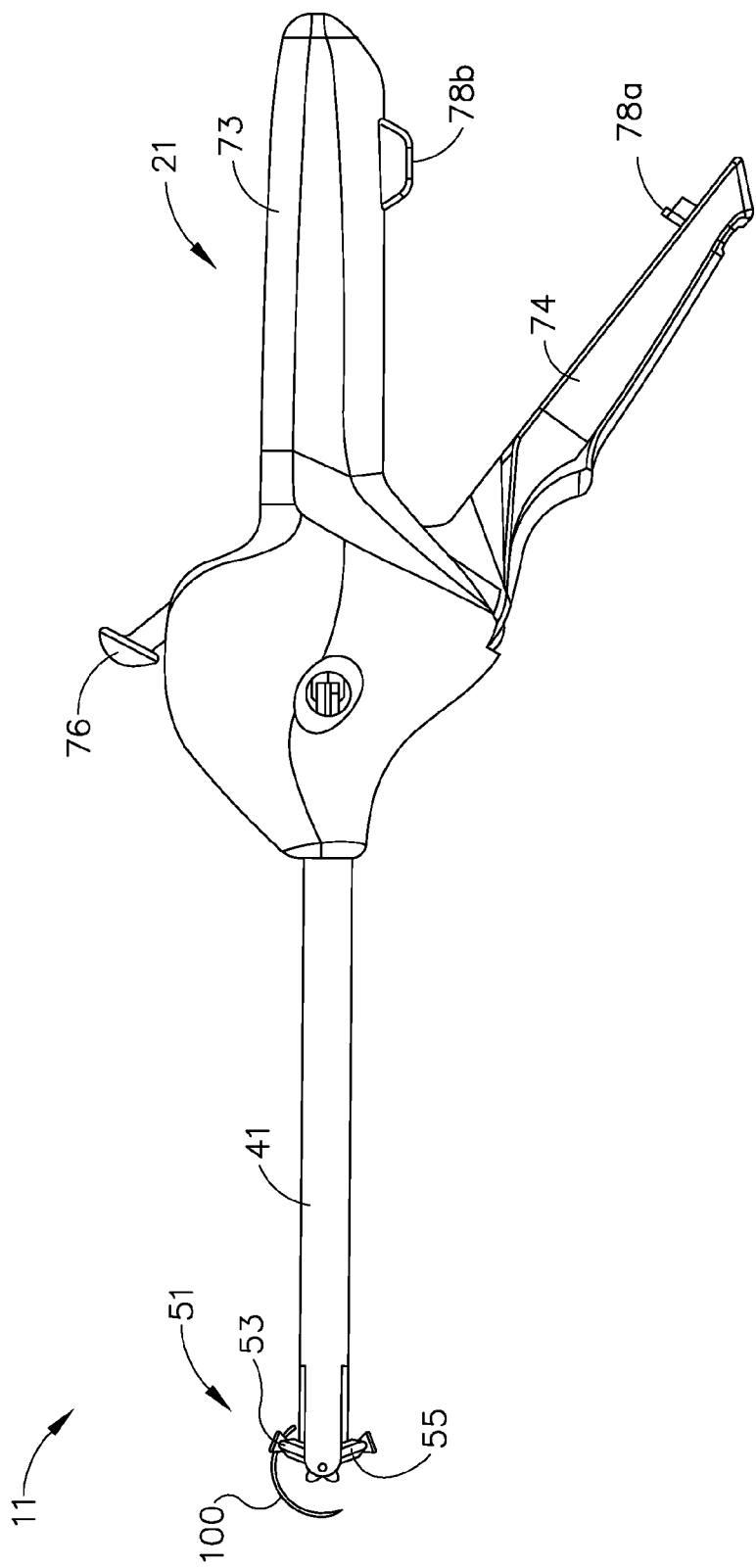
FIG. 3 depicts a side elevational view of an exemplary alternative laparoscopic suturing instrument.

FIG. 3 depicts a merely illustrative alternative example of a suturing instrument (11). Instrument (11) of this example includes a handle portion (21), a shaft (41) extending distally from handle portion (21), and an end effector (51) at the distal end of shaft (41). Handle portion (21) includes a fixed grip (72), a pivoting grip (74), and a button (76). Pivoting grip (74) and button (76) are each resiliently biased to the positions shown in FIG. 4, such as by one or more springs, etc. Pivoting grip (74) and button (76) may each be pushed toward fixed grip (72) to actuate features of end effector (51). Various other suitable components, features, and configurations for handle portion (20) will be apparent to those of ordinary skill in the art in view of the teachings herein.

Shaft (41) of the present example has an outer diameter sized to permit shaft (41) to be inserted through a conventional trocar (not shown). Shaft (41) also has a length sized to permit end effector (51) to be positioned at a surgical site within a patient while also allowing handle portion (21) to be manipulated by a user (e.g., a surgeon) from a location outside the patient when shaft (41) is disposed in a trocar. Of course, shaft (41) need not necessarily be dimensioned for use through a trocar. For instance, instrument (10) may be used and/or configured for use in open surgical procedures.

In some versions, shaft (41) includes one or more articulating features, allowing end effector (51) to be articulated to various angles and positions relative to the longitudinal axis defined by shaft (41). Merely illustrative examples of such articulation are taught in U.S. Provisional Application Ser. No. 61/355,832, the disclosure of which is incorporated by reference herein. Various other suitable ways in which articulation may be provided will be apparent to those of ordinary skill in the art in view of the teachings herein. In addition or in the alternative, shaft (41) may be rotatable about the longitudinal axis, relative to handle portion (21), to selectively position end effector (51) at various angular orientations about the longitudinal axis. Of course, a user may rotate the entire instrument (11) about the longitudinal axis to selectively position end effector (51) at various angular orientations about the longitudinal axis.

End effector (51) of the present example includes a first arm (53) and a second arm (55). Arms (53, 55) are configured to alternatingly throw and catch a curved suturing needle (100) along a path that is substantially parallel to the longitudinal axis defined by shaft (41). Alternatively, arms (53, 55) may be configured to alternatingly throw and catch needle (100) along a path that is substantially perpendicular to the longitudinal axis defined by shaft (41); or along some other path. In addition, arms (53, 55) of the present example pass needle (100) back and forth from arm (53) to arm (55) and from arm (55) to arm (53) in an oscillating motion (i.e., back and forth in opposite directions), such that needle (100) does not traverse a circular path as needle (100) is being passed between arms (53, 55). By way of example only, arms (53, 55) may move in accordance with at least some of the teachings of U.S. Provisional Patent Application No. 61/355,832, the disclosure of which is incorporated by reference herein; and/or in accordance with at least some of the teachings of U.S. patent application Ser. No. 13/156,420, a published as U.S. Pub No. 2011/0313433 on Dec. 22, 2011, now U.S. Pat. No. 9,168,037, issued on Oct. 27, 2015, the disclosure of which is incorporated by reference herein.

Arms (53, 55) are operatively coupled with pivoting grip (74) and button (76). In particular, pivoting grip (74) is operable to move arms (53, 55) toward each other when pivoting grip (74) is squeezed toward fixed grip (72). In some versions, handle portion (21) includes a rack and pinion configuration, with a translating member moving within shaft (41), and a camming feature at end effector (51) to provide such movement of arms (53, 55) in response to actuation of pivoting grip (74). Merely illustrative examples of such features are taught in U.S. Provisional Patent Application Ser. No. 61/355,832, the disclosure of which is incorporated by reference herein. In addition or in the alternative, one or more motors may be coupled with pivoting grip (74) and/or another user input feature to selectively drive one or both of arms (53, 55). In some versions, a single motor is operable to selectively drive one or both of arms (53, 55) to pass needle (100) between arms, including selectively grasping and releasing needle (100) among arms (53, 55) in the appropriate sequence, in response to activation of one or more user input features. Various other suitable ways in which movement of arms (53, 55) may be provided in response to actuation of pivoting grip (74) and/or some other user input feature will be apparent to those of ordinary skill in the art in view of the teachings herein. As noted above, pivoting grip (74) is resiliently biased to the position shown in FIG. 3. Pivoting grip (74) and fixed grip (72) include complementary latching features (78a, 78b) that are operable to selectively lock pivoting grip (74) to an actuated position where grips (72, 74) are adjacent and parallel with each other. As with other features described herein, latching features (78a, 78b) are merely optional and may be modified, substituted, supplemented, or omitted as desired.

In the present example, as arms (53, 55) throw and catch needle (100) to each other, arms (53, 55) move toward and away from each other (and toward and away from the longitudinal axis defined by shaft (30)) in a synchronous manner. Button (76) is used to actuate features in arms (53, 55) to selectively grip and release needle (100). For instance, when arms (53, 55) are approximated, button (26) may be actuated to simultaneously release needle (100) from arm (53) and grip needle (100) with arm (55). Examples of various suitable components, features, and configurations that may be used to provide such selective gripping of needle (100) by arms (53, 55) are taught in U.S. Provisional Application Ser. No. 61/355,832, the disclosure of which is incorporated by reference herein; and U.S. patent application Ser. No. 13/295,203, issued as U.S. Pat. No. 8,702,732 on Apr. 22, 2014, the disclosure of which is incorporated by reference herein. Still other suitable components, features, and configurations that may be used to provide selective gripping of needle (100) by arms (53, 55) will be apparent to those of ordinary skill in the art in view of the teachings herein. Similarly, other variations of instruments (10, 11) and ways in which suturing instruments may be used with needle (100) will be apparent to those of ordinary skill in the art in view of the teachings herein.

II. Exemplary Needle Configurations

FIGS. 4-32 depict various examples of needle configurations as will be described in greater detail below. While needle (100) is referred to specifically in the examples described above, it should be understood that any of the various needles described below may be readily used with instruments (10, 11) as described above, with a suturing instrument as described in any of the references cited herein, and/or with numerous other kinds of suturing instruments. Various suitable ways in which the needles described below may be used with a suturing instrument will be apparent to those of ordinary skill in the art in view of the teachings herein. It should also be understood that the various needles described herein may be constructed using various techniques. By way of example only, various needles described herein may be constructed using metal-injection-molding (MIM) processes. The needles may also be formed as sheets, wires, tubes, extrusions, or other components that are bent, stamped, coined, milled, otherwise machined, and/or otherwise formed. Other suitable ways in which needles may be constructed will be apparent to those of ordinary skill in the art in view of the teachings herein.

Some of the examples of needles described below include a single sharp tip and an opposing blunt tip. It should be understood that such examples may be readily modified to include sharp tips at both ends of the needle. Likewise, examples described below that include a sharp tip at each end may be readily modified to include a sharp tip at just one end and a blunt tip at the other end. While some examples described below include just a single strand of suture extending from the needle, it should be understood that such examples may be readily modified to have two or more strands extending from the needle (e.g., double leg suture, etc.). It should also be understood that sutures as referred to herein may include conventional smooth sutures, barbed sutures, and/or any other suitable kinds of sutures. Still other suitable variations and combinations of the following teachings will become apparent to those of ordinary skill in the art.

A. Exemplary Solid Needle with Oblique Suture Passage

FIGS. 4-9 depict an exemplary needle (100) that includes a sharp tip (110), a blunt end (120), a suture passage (130), a distal grasping region (140), and a proximal grasping region (150). As will be described in greater detail below, sharp tip (110) is configured to pierce and penetrate tissue. Blunt end (120) is substantially flat in the present example, though it should be understood that blunt end (120) may have various other configurations, including but not limited to rounded, sharp, etc. Grasping regions (140, 150) are configured to facilitate grasping of needle (100) by arms of a suturing instrument such as instrument (10) described above. In the present example, grasping regions (140, 150) comprise concave grooves or scallops formed into the convex curvature of needle (100). In other words, the plane of curvature for grasping regions (140, 150) is common with the plane of curvature for needle (100). Of course, grasping regions (140, 150) may have a variety of other configurations, including but not limited to the configuration described below with respect to FIG. 11. Needle (100) of the present example also includes substantially flat sides (122). The flat configuration of sides (122) may further assist in proper alignment of needle (100) along a plane of travel as needle (100) is passed from one arm of a suturing instrument to another arm of a suturing instrument. It should be understood that a flat configuration may be provided along any portion of the length of sides (122); or that sides (122) may have any other suitable configuration. It should also be understood that the configuration of grasping regions (140, 150) may also assist in proper alignment of needle (100) along a plane of travel as needle (100) is passed from one arm of a suturing instrument to another arm of a suturing instrument.

Figure 4:
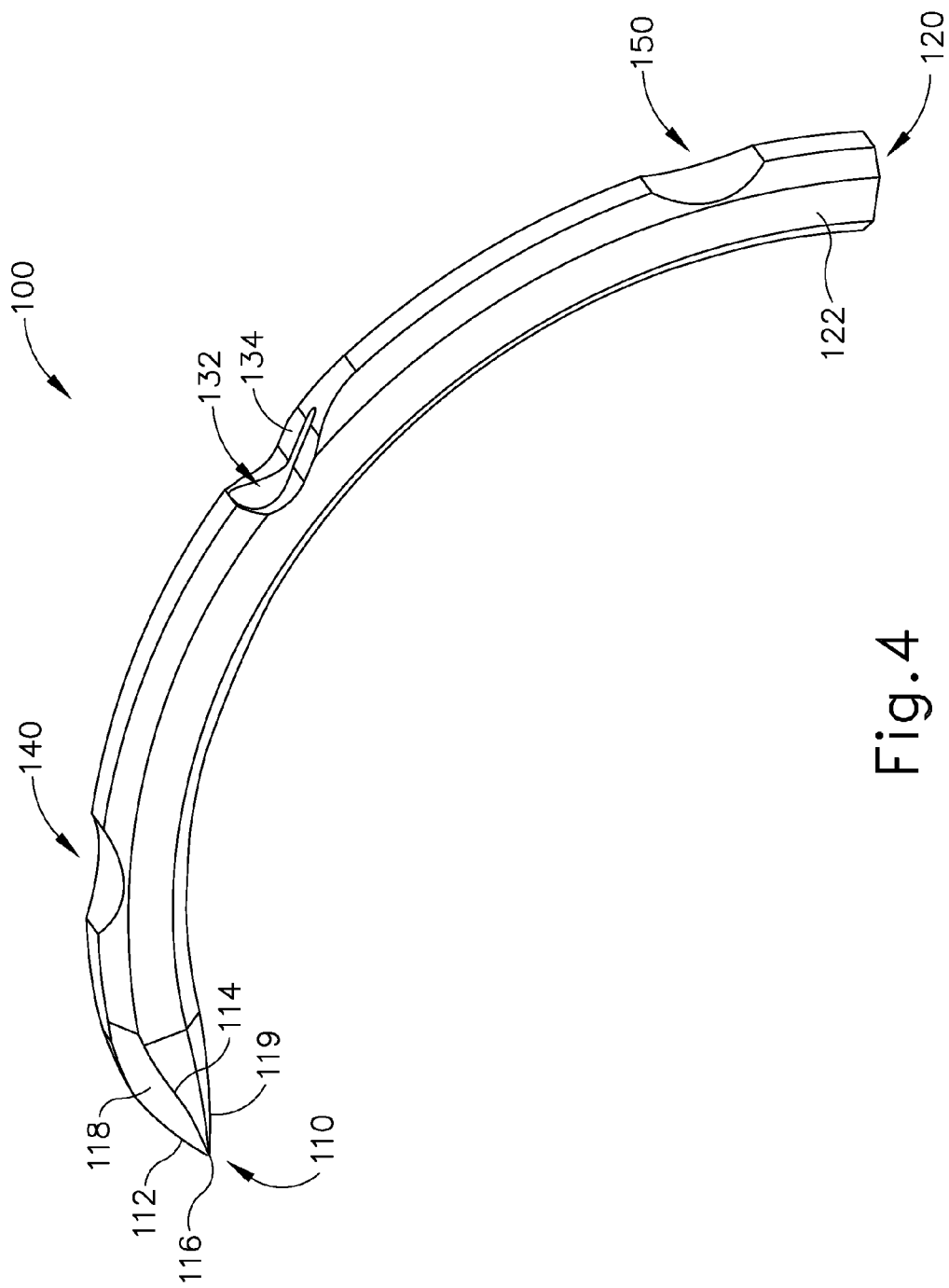
FIG. 4 depicts a perspective view of an exemplary suturing needle.
Figure 5:
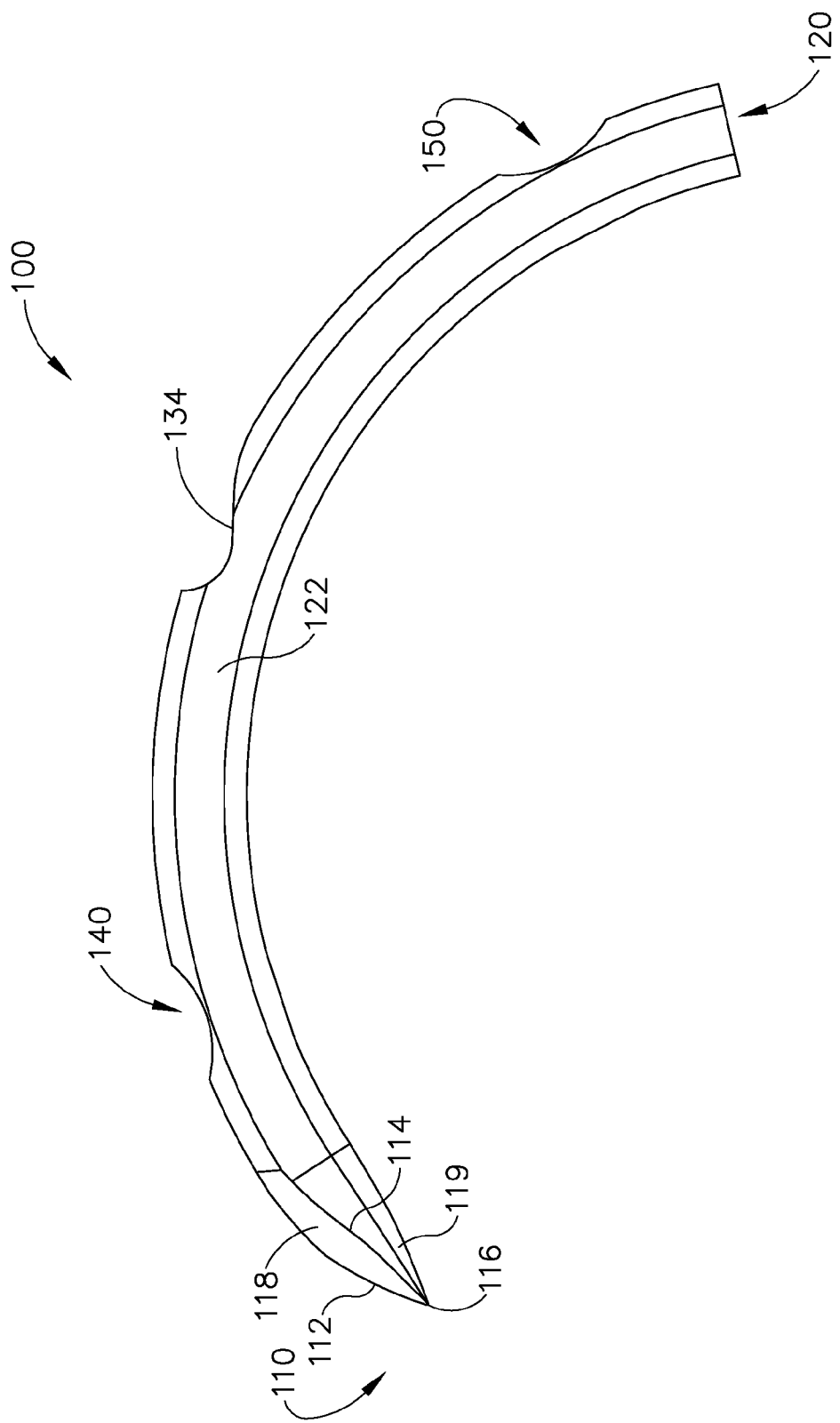
FIG. 5 depicts a side elevational view of the needle of FIG. 4.
Figure 6:
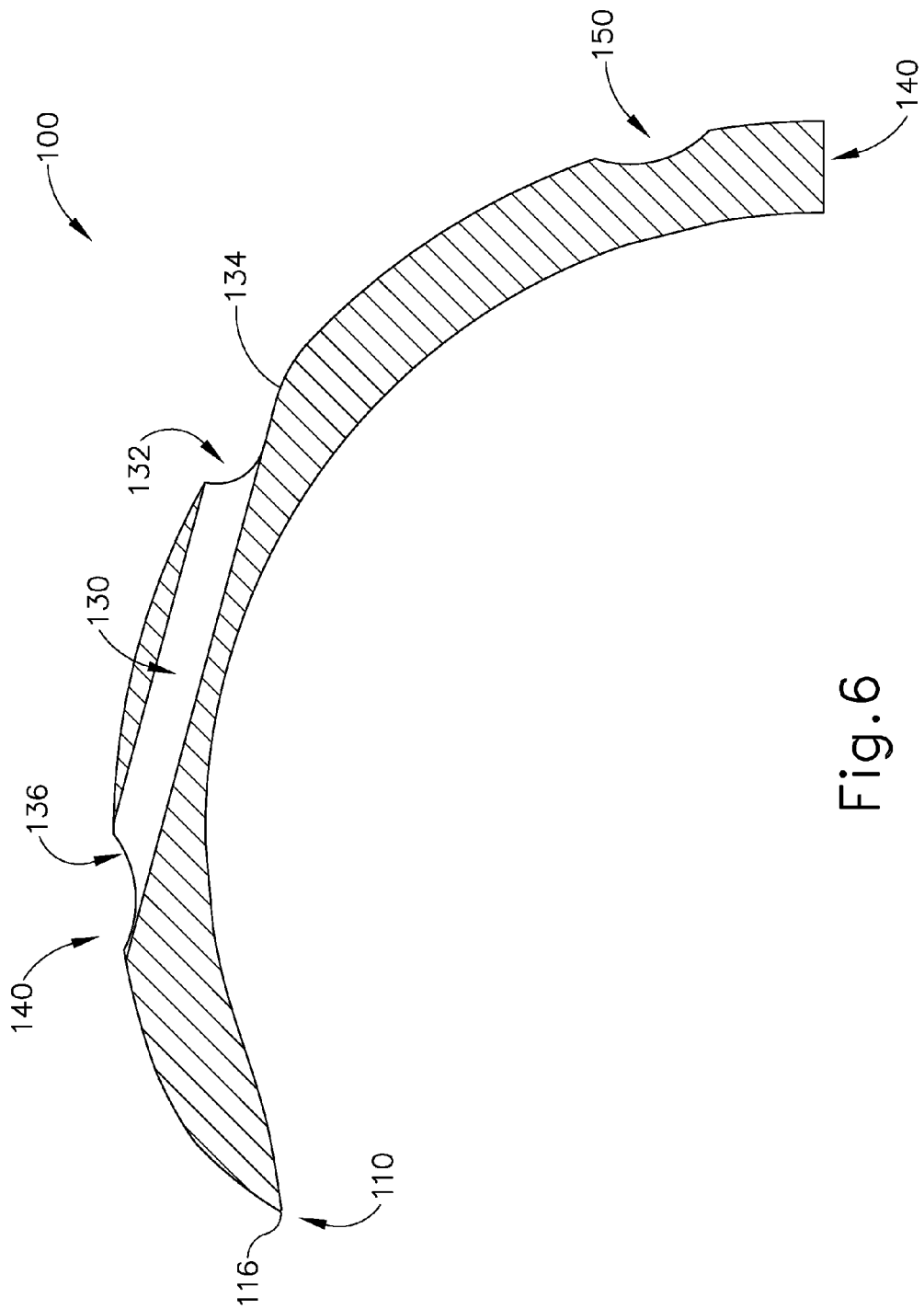
FIG. 6 depicts a side cross-sectional view of the needle of FIG. 4.
Figure 7:
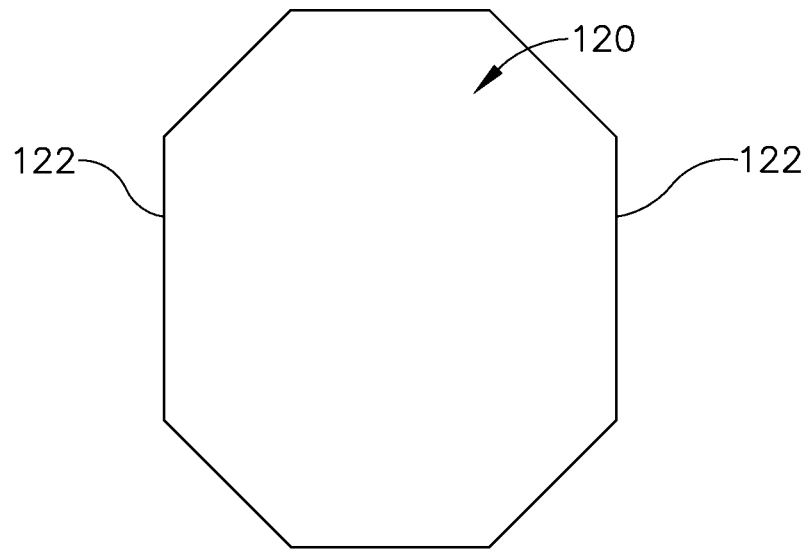
FIG. 7 depicts an end view of the blunt end of the needle of FIG. 4.

As best seen in FIGS. 4 and 6, suture passage (130) proximally terminates at a proximal opening (132), which is oriented at an oblique angle relative to the curved centerline along which needle (100) extends. This angle is complemented by a ramped surface (134) that is adjacent to proximal opening (132). Suture passage (130) distally terminates at a distal opening (136), which is formed at distal grasping region (140). However, it should be understood that distal opening (136) need not necessarily be formed at distal grasping region (140). As another merely illustrative variation, suture passage (130) may distally terminate at an internal wall inside needle (100), such that suture passage (130) dead ends within needle (100). Suture passage (130) is configured to receive a suture (not shown). A suture that is inserted within suture passage (130) may be secured relative to needle (100) in numerous ways as will be apparent to those of ordinary skill in the art in view of the teachings herein. Such securing methods may include crimping needle (100) onto the suture, using an adhesive, using a separate clip, using ultrasonic welding, and/or using various other structures/techniques/etc.

It should be understood that a suture inserted in suture passage (130) may exit proximal opening (132) at an angle that is tangent to the curve of needle (100), without the suture bending at proximal opening (132). Alternatively, the suture exiting suture passage (130) may exit at an angle that is oblique relative to the curve of needle (100). In either case, by exiting at a non-perpendicular angle relative to needle (100), the suture may provide less drag force than might otherwise be provided if suture exited needle (100) at a substantially perpendicular angle. Furthermore, when needle (100) pulls the suture through tissue, the orientation of the suture may provide less tissue trauma than would otherwise be provided if the suture exited needle (100) at a substantially perpendicular angle. It should also be understood that the orientation of suture passage (130) relative to the curvature of needle (100) may have relatively minimal impact on the structural integrity of needle (100). For instance, if suture passage (130) were oriented substantially perpendicular to the curvature of needle (100), needle (100) may be more likely to snap if tip (110) were driven into a hard surface or if needle (100) were bent along a path substantially transverse to the length of needle (100).

Figure 8:
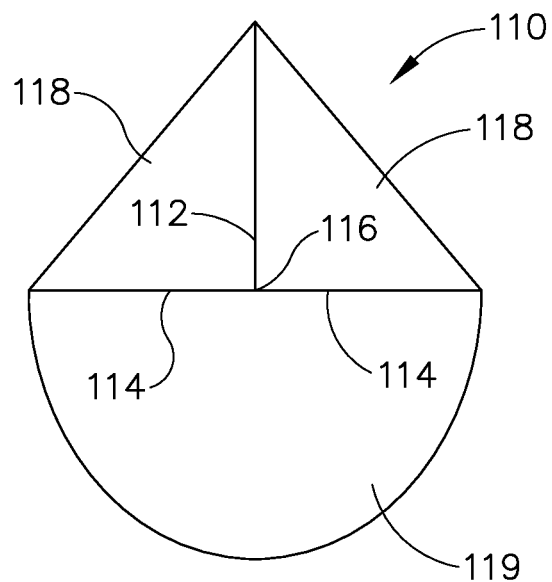
FIG. 8 depicts an end view of the pointed end of the needle of FIG. 4.
Figure 9:
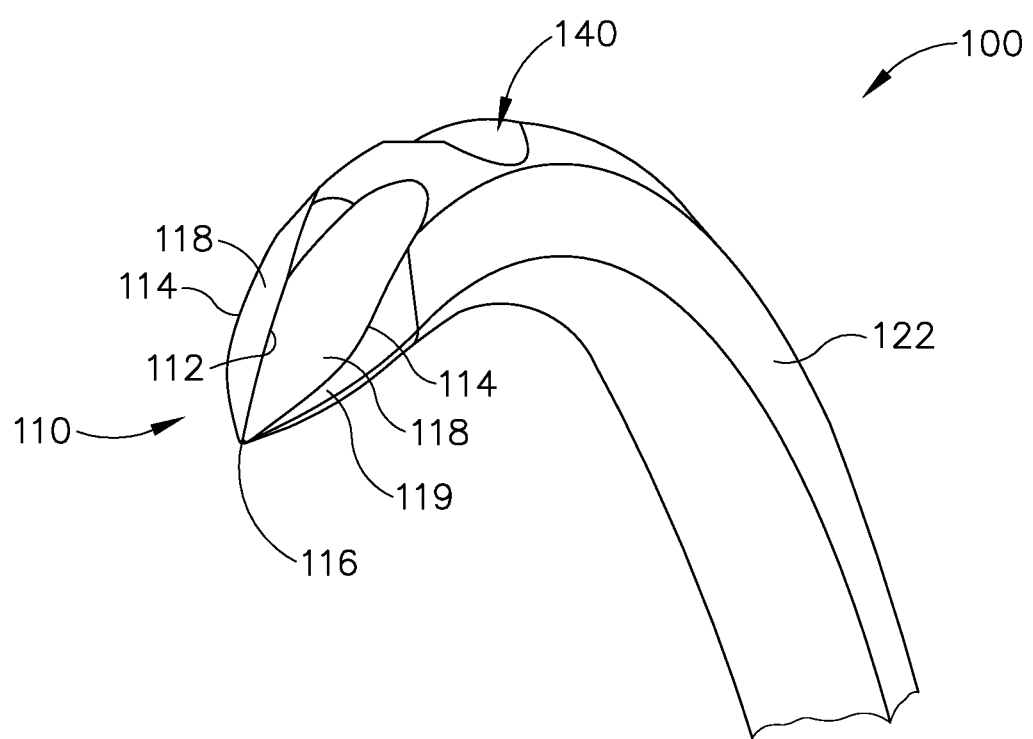
FIG. 9 depicts a partial perspective view of the pointed end of the needle of FIG. 4.

FIGS. 8-9 depict tip (110) of the present example in greater detail. As shown, tip (110) includes a pair of substantially flat surfaces (118) bounded by a common sharp edge (112) and respective lateral sharp edges (114). Edges (112, 114) terminate in a sharp point (116). A convexly curved surface (119) extends under edges (114), along the inside of the curve defined by needle (100). Curved surface (119) tapers toward point (116). It should be understood that the configuration of tip (110) may provide tissue penetration with force requirements that are substantially lower than force requirements for conventional needle tips. The configuration of tip (110) may also provide relatively less tissue trauma than might otherwise be provided by conventional needle tips. Alternatively, tip (110) may have any other suitable configuration. It should also be understood that blunt end (140) may be substituted with sharp tip (110). Furthermore, any other needle described herein may have one or more sharp tips constructed in accordance with tip (110). In one merely illustrative variation, flat surfaces (118) are substituted with hollow ground surfaces. Other suitable variations for tip (110) will be apparent to those of ordinary skill in the art in view of the teachings herein.

Figure 10:
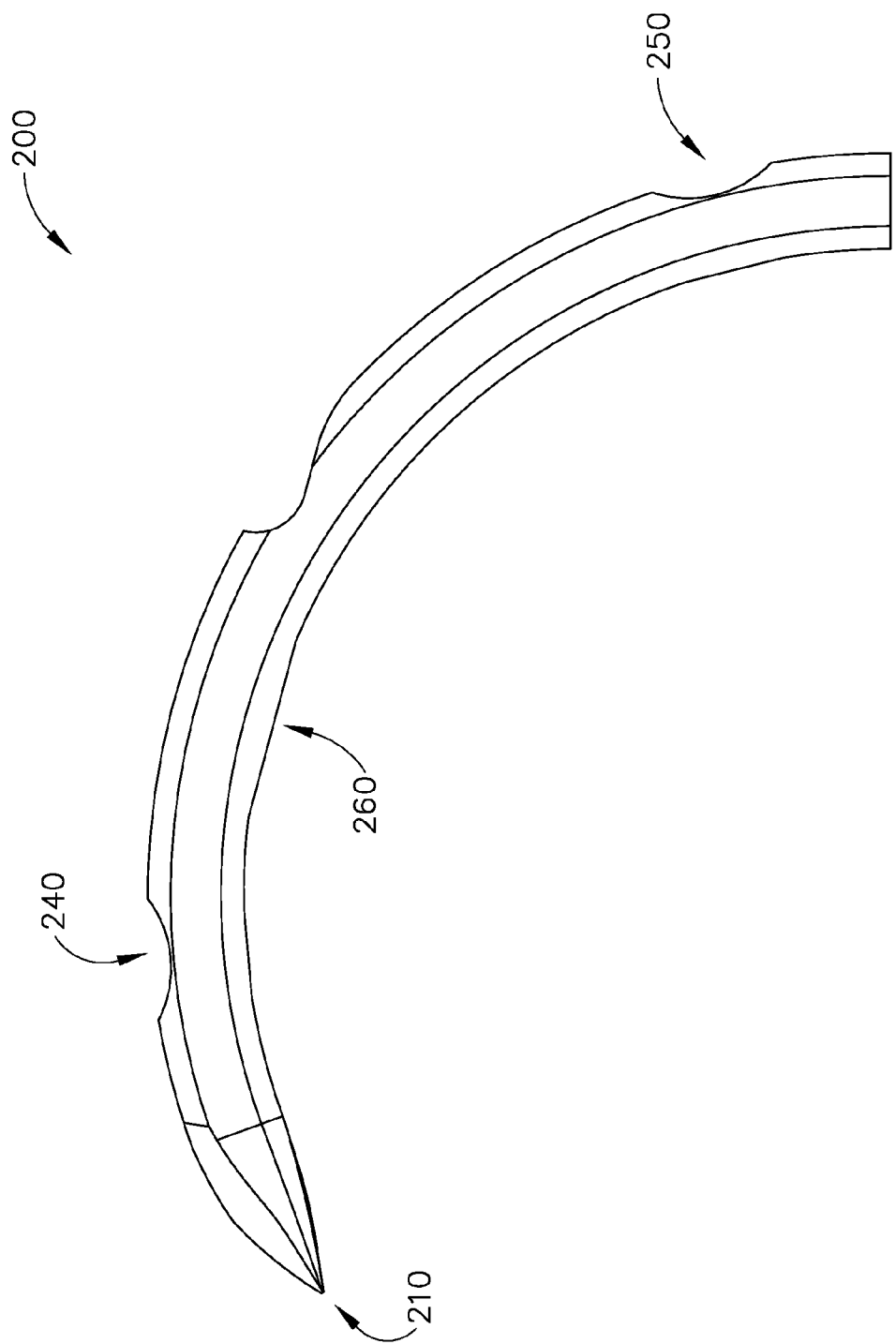
FIG. 10 depicts a side elevational view of an exemplary alternative suturing needle.

FIG. 10 depicts an exemplary variation of needle (100). In this example, needle (200) includes a sharp tip (210), a pair of grasping regions (240, 250), and an area (260) of increased thickness. Needle (200) is otherwise substantially similar to needle (100) described above. Area (260) is located proximal to grasping region (240) in this example. It should be understood that area (260) may be located elsewhere along the length of needle (200). In versions where needle (200) is hollow, area (260) may extend into the interior of needle such that the increase in wall thickness does not affect the outer profile of needle (200). It should also be understood that needle (200) may include a plurality of areas (260) at various suitable locations along the length of needle (200). The increased thickness of area (260) provides improved structural integrity in this example. Thus, the presence of area (260) may further reduce the likelihood that needle (200) will snap if tip (210) were driven into a hard surface or if needle (200) were bent along a path substantially transverse to the length of needle (200).

Figure 11:
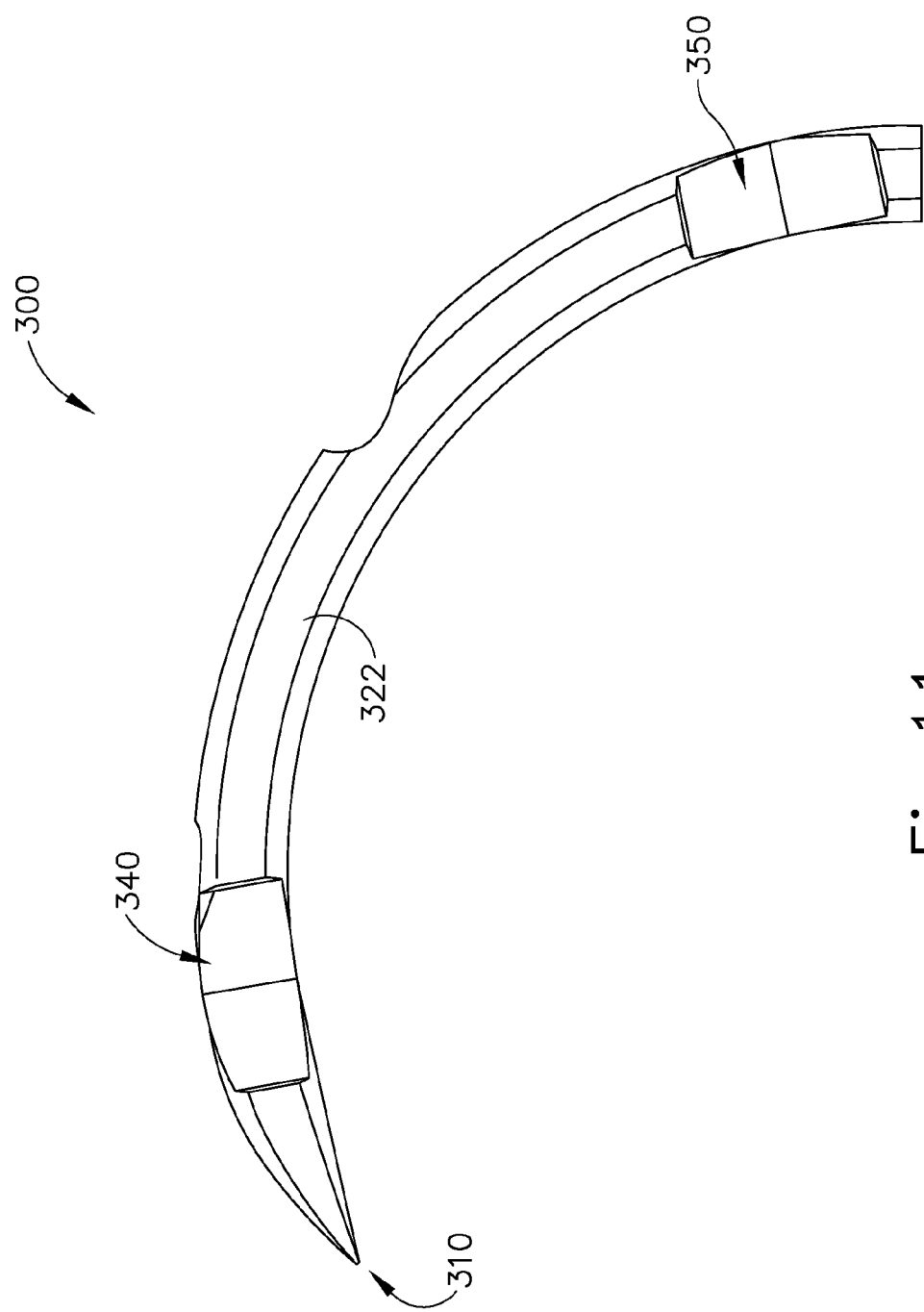
FIG. 11 depicts a side elevational view of another exemplary alternative suturing needle.

FIG. 11 depicts another exemplary variation of needle (100). In this example, needle (300) includes a sharp tip (310) and a pair of grasping regions (340, 350). Needle (300) is configured substantially similar to needle (100) described above, except that grasping regions (340, 350) of needle (300) are formed in the lateral side (322) of needle (300). Grasping regions (340, 350) comprise concave scallops or grooves formed lateral to the convex curvature of needle (300). In other words, the plane of curvature for each grasping region (340, 350) is perpendicular to the plane of curvature for needle (300). In the present example, grasping regions (340, 350) are provided on just one lateral side (322) of needle (300). In some other versions, grasping regions (340, 350) are each provided in pairs on opposing sides (322) of needle (300). Still other suitable configurations and arrangements will be apparent to those of ordinary skill in the art in view of the teachings herein.

B. Exemplary Hollow Needle with Oblique Suture Passage

Figure 12:
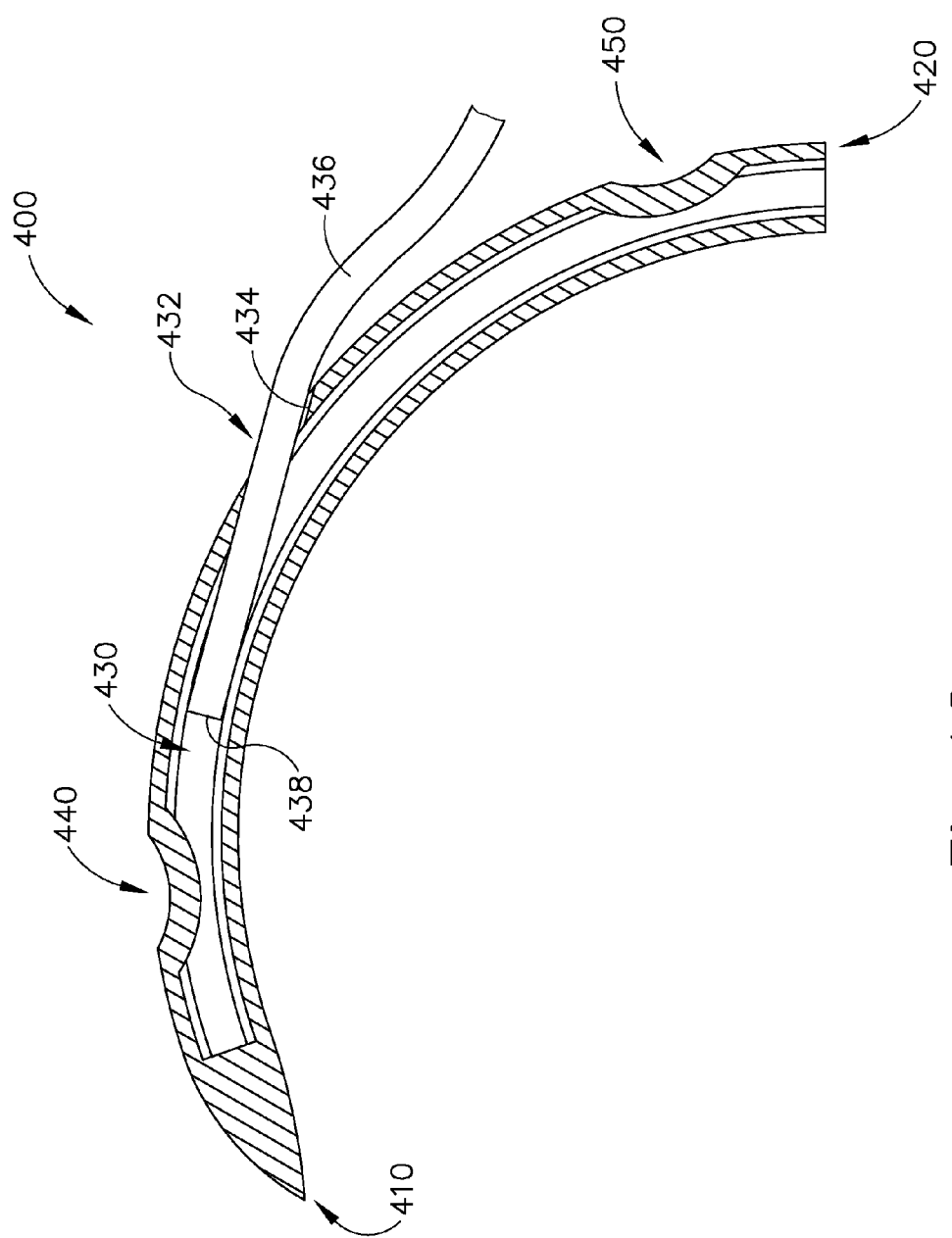
FIG. 12 depicts a side cross-sectional view of another exemplary alternative suturing needle.
Figure 13:
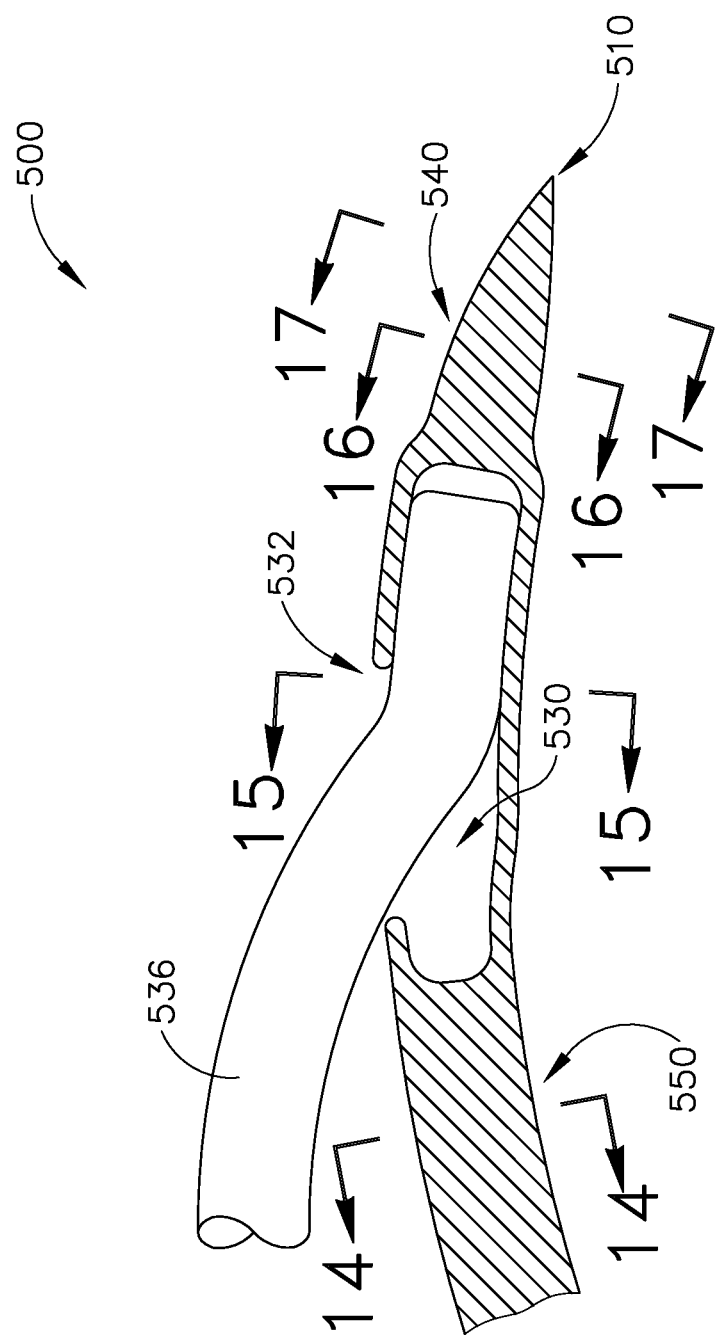
FIG. 13 depicts a side cross-sectional view of another exemplary alternative suturing needle.

FIG. 12 depicts an exemplary needle (400) that includes a sharp tip (410), a blunt end (420), a hollow interior (430), a distal grasping region (440), and a proximal grasping region (450). Needle (400) of this example comprises a formed hypodermic tube or "hypo tube." Those of ordinary skill in the art should recognize that "hypo tube" is a term used to refer to a surgical grade small diameter tube that may be used to form a hypodermic needle and/or other medical components that are configured to pass through tissue. Of course, needle (400) may be formed from any other type of tubular structure and/or using any other suitable techniques. Sharp tip (410) of the present example is formed by crimping and/or machining the distal end of the hypo tube to ultimately yield a configuration similar to that described above for sharp tip (110). Alternatively, sharp tip (410) may be provided by a molded (or otherwise formed) piece that is coupled with the distal end of the hypo tube. Other suitable configurations for sharp tip (410) will be apparent to those of ordinary skill in the art in view of the teachings herein. While blunt end (420) is open in the present example, it should be understood that blunt end (420) may instead be closed.

Grasping regions (440, 450) are formed by crimping the hypo tube. Alternatively, grasping regions (440, 450) may be formed in any other suitable fashion. Grasping regions (440, 450) of this example are substantially similar in configuration and function as grasping regions (140, 150) described above. While not shown, needle (400) may also include substantially flat lateral sides, similar to sides (122) described above.

A suture opening (432) is in communication with hollow interior (430), and is oriented at an oblique angle relative to the curved centerline along which needle (400) extends. This angle is complemented by a ramped surface (434) that is adjacent to suture opening (432). As shown, a suture (436) is inserted into hollow interior (430) via suture opening (432). The distal end (438) of suture (436) may be secured relative to needle (400) in numerous ways as will be apparent to those of ordinary skill in the art in view of the teachings herein, including but not limited to crimping needle (400) onto the suture (436), using an adhesive, using a separate clip, using ultrasonic welding, and/or using various other structures/techniques/etc. While distal end (438) of suture (436) is shown as being located proximal to distal grasping region (440), distal end (438) may be located at any other suitable position. In some versions, distal end (438) of suture (436) is located at or distal to the region associated with the underside of distal grasping region (440), then distal grasping region (440) is formed by crimping the hypo tube against suture (436), such that the underside of distal grasping region (440) effectively grips suture (436).

As shown in FIG. 12, suture (436) exits suture opening (432) at an angle that is generally tangent to the curve of needle (400), without the suture bending at proximal opening (432). Alternatively, suture (436) may exit hollow interior (430) at an angle that is oblique relative to the curve of needle (400). In either case, by exiting at a non-perpendicular angle relative to needle (400), suture (436) may provide less drag force than might otherwise be provided if suture (436) exited needle (400) at a substantially perpendicular angle. Furthermore, when needle (400) pulls suture (436) through tissue, the orientation of suture (436) may provide less tissue trauma than would otherwise be provided if suture (436) exited needle (400) at a substantially perpendicular angle. It should also be understood that the orientation of suture opening (432) relative to the curvature of needle (400) may have relatively minimal impact on the structural integrity of needle (400). For instance, if suture opening (432) were oriented substantially perpendicular to the curvature of needle (400), needle (400) may be more likely to snap if tip (410) were driven into a hard surface or if needle (400) were bent along a path substantially transverse to the length of needle (400). Still other suitable components, features, and configurations that may be incorporated into needle (400) will be apparent to those of ordinary skill in the art in view of the teachings herein.

C. Exemplary Needle Formed from Crimped Sheet

FIGS. 13-17 depict an exemplary needle (500) that comprises a sharp tip (510), a suture recess (530), a distal grasping region (540), and a proximal grasping region (550). Needle (500) of this example is formed from micro-stamped sheet metal, through a process of folding, crimping, bending, and/or machining For instance, a piece of micro-stamped sheet metal may first be folded to provide a generally elongate, generally rigid structure. A die or other component may be used to form suture recess (530) during this part of the process. The structure may then be crimped to form grasping regions (540, 550) and to form part of sharp tip (510). A machining process may be used to finish sharp tip (510). The structure may then be bent to provide needle (500) in a curved form. Each of the above described features of needle (500) will be described in greater detail below. It should be understood that needle (500) may include various other features and/or may be formed using various other types of processes.

Sharp tip (510) of the present example is formed by crimping and/or machining the distal end of needle (500) to ultimately yield a configuration similar to that described above for sharp tip (110). Other suitable configurations for sharp tip (510) will be apparent to those of ordinary skill in the art in view of the teachings herein. It should also be understood that needle (500) may include a proximal end that is blunt, sharp, or otherwise configured.

As best seen in FIGS. 14 and 16, grasping regions (540, 550) are formed by squeezing the body of needle (500), creating opposing flat sides (542, 552). Flat sides (542, 552) each run along only a portion of the length of needle (500). In some versions, grasping regions (540, 550) are substantially similar in configuration and function as grasping regions (140, 150) described above, except that grasping regions (540, 550) of this example are formed on the sides of needle (500) and are formed as opposing recesses. In some other versions, grasping regions (540, 550) are formed on the bottom side and/or top side of needle (500), similar to grasping regions (140, 150). It should also be understood that each grasping region (540, 550) may consist of a single recess instead of comprising a pair of opposing recesses. Still other suitable configurations and arrangements for grasping regions (540, 550) will be apparent to those of ordinary skill in the art in view of the teachings herein.

Suture recess (530) is in communication with an elongate suture opening (532). A suture (536) is disposed in suture recess (530) via suture opening (532). The distal end (538) of suture (536) may be secured relative to needle (500) in numerous ways as will be apparent to those of ordinary skill in the art in view of the teachings herein, including but not limited to crimping needle (500) onto the suture (536), using an adhesive, using a separate clip, using ultrasonic welding, and/or using various other structures/techniques/etc. In the present example, suture (536) exits opening (532) at an angle that is generally tangent to the curve of needle (500), without the suture bending significantly at proximal opening (532). Alternatively, suture (536) may exit hollow suture recess (530) at an angle that is oblique relative to the curve of needle (500). In either case, by exiting at a non-perpendicular angle relative to needle (500), suture (536) may provide less drag force than might otherwise be provided if suture (536) exited needle (500) at a substantially perpendicular angle. Furthermore, when needle (500) pulls suture (536) through tissue, the orientation of suture (536) may provide less tissue trauma than would otherwise be provided if suture (536) exited needle (500) at a substantially perpendicular angle. Still other suitable components, features, and configurations that may be incorporated into needle (500) will be apparent to those of ordinary skill in the art in view of the teachings herein.

D. Exemplary Needle with Central Suture Wrap

Figure 18:
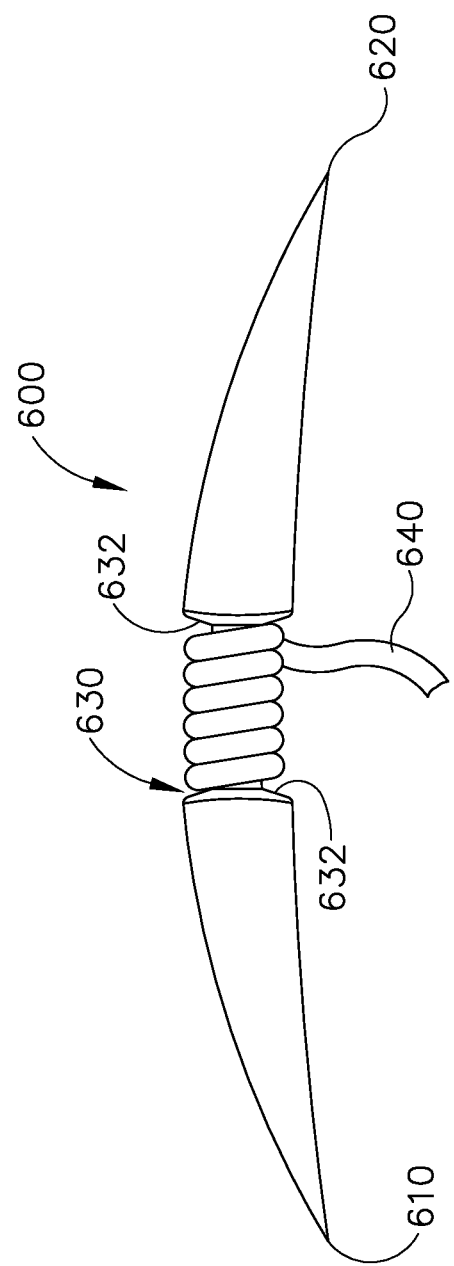
FIG. 18 depicts a side elevational view of another exemplary alternative suturing needle.

FIG. 18 depicts an exemplary needle (600) having an opposing pair of sharp tips (610, 620), a recessed central region (630), and a suture (640) wrapped about recessed central region (630). Sharp tips (610, 620) may be configured in accordance with sharp tip (110) described above; or may be otherwise configured. In the present example, needle (600) is formed by a single unitary piece (e.g., a single piece of metal), with recessed central region (630) being a machined (e.g., lathed, ground, etc.), molded, or otherwise formed feature of the single unitary piece. In some other versions, needle (600) is formed by two end pieces that respectively include tips (610, 620) and that are joined to a bar or other structure that forms central region (630). Any other suitable components, configurations, or arrangements may be used.

As noted above, suture (640) is wrapped about central region (630). In some versions, the friction provided by suture (640) being wrapped about itself is sufficient to secure suture (640) to central region (630). In addition or in the alternative, suture (640) may be knotted, welded, glued, clipped, or otherwise secured to central region (630). In some versions where central region (630) is provided by a separate piece, suture (640) is captured between the central region (630) piece and one or both of the end pieces that include sharp tips (610, 620). Alternatively, suture (640) may be secured to needle (600) in any other suitable fashion. In the present example, the suture-on-suture interface provided by the portion of suture (640) that is wrapped about central region (630) provides greater flexibility for suture (640) to exit needle (600) along a path that is generally tangential to or otherwise oblique relative to needle (600). Such tangential or oblique exit may provide reduced drag forces and/or reduced tissue trauma, as described above. It should also be understood that the recessed configuration of central region (630) may provide reduced drag forces and/or reduced tissue trauma as needle (600) is pulled through tissue. In other words, the wrapped portion of suture (640) does not extend outside the outer perimeter defined by needle (600) in the present example. In addition, needle (600) of this example includes chamfered transition regions (632) leading to central region (630). The chamfered configuration of transition regions (632) may further provide reduced drag forces and/or reduced tissue trauma as compared to what might otherwise be provided if the transition were square or otherwise configured.

FIGS. 19-20 depict a variation where needle (700) includes an opposing pair of sharp tips (710, 720), a recessed central region (730), and a suture (740) secured to recessed central region (730). Needle (700) of this example is substantially identical to needle (600) described above, except that recessed central region (730) of this example includes a plurality of transverse passages (734). Transverse passages (734) are all parallel with each other in this example, though it should be understood that transverse passages may be oriented obliquely relative to each other. It should also be understood that one or more transverse passages (734) may be skewed relative to one or more other transverse passages (734). In the present example, suture (740) is weaved through passages (734) to secure suture (740) to needle (700). This weaving of suture (740) may suffice to secure suture (740) to needle (700) in some instances. In addition or in the alternative, suture (740) may be knotted, welded, glued, clipped, or otherwise secured to central region (730).

It should be understood that the recessed configuration of central region (730) may provide reduced drag forces and/or reduced tissue trauma as needle (700) is pulled through tissue. In other words, the weaved portion of suture (740) does not extend outside the outer perimeter defined by needle (700) in the present example. In addition, needle (700) of this example includes chamfered transition regions (732) leading to central region (730). The chamfered configuration of transition regions (732) may further provide reduced drag forces and/or reduced tissue trauma as compared to what might otherwise be provided if the transition were square or otherwise configured. Of course, either needle (600, 700) described above may also include one or more features (not shown) to facilitate grasping of needle (600, 700). Still other suitable components, features, configurations, and relationships for needles (600, 700) and sutures (640, 740) will be apparent to those of ordinary skill in the art in view of the teachings herein.

E. Exemplary Needle with Pivoting Suture Ball Joint

FIGS. 21-23 depict an exemplary needle (800) that includes an opposing pair of sharp tips (810, 820), and a central recess (830). While not shown, it should be understood that needle (800) may also include one or more features to facilitate grasping of needle (800). By way of example only, such features may be configured similar to grasping regions (540, 550) shown in FIGS. 14 and 16. As with any other sharp tip referred to herein, sharp tips (810, 820) may be configured in accordance with the above teachings relating to tip (110) and/or in any other suitable fashion. Central recess (830) may be formed using any suitable processes, including but not limited to MIM, folding around a die, milling, etc. Central recess (830) is configured to receive a ball (850) at the end of a suture (860). Ball (850) of the present example is fixedly secured to the end of suture (860). For instance, ball (850) may be crimped about the end of suture (860), may be adhered to suture (860), may be overmolded about suture (860), and/or may be secured to suture (860) in any other suitable fashion. Ball (850) may be formed of any suitable material, including but not limited to metal, plastic, etc. Ball (850) may also be formed through various kinds of microfabrication processes and/or other types of processes. By way of example only, ball (850) and/or at least a portion of suture (860) may be formed in accordance with at least some of the teachings of U.S. Pub. No. 2011/0054522, entitled "Barbed Sutures Having Pledget Stoppers and Methods Therefor," published Mar. 3, 2011, issued as U.S. Pat. No. 9,011,487 on Apr. 21, 2015, the disclosure of which is incorporated by reference herein; and/or U.S. Pub. No. 2008/0161850, entitled "Suture Anchoring System," published Jul. 3, 2008, now abandoned, the disclosure of which is incorporated by reference herein. As another merely illustrative example, ball (850) may be formed as a melted knot at the end of suture (860).

Needle (800) retains ball (850) in this example with localized crimps (832) formed adjacent to central recess (830). The relationship between ball (850) and needle (800) nevertheless enables ball (850) to pivot and rotate within central recess (830), similar to a ball and socket type of joint. A pair of opposing elongate slots (834) adjacent to crimps (832) provide further clearance for suture (860) as suture (860) and ball (850) are pivoted to positions where suture (860) is oriented substantially tangential or obliquely relative to needle (800). As noted above, providing a substantially non-perpendicular angle of exit for suture (860) relative to needle (800) may result in reduced drag forces and/or reduced tissue trauma as compared to a configuration where suture (860) exits needle (800) at a substantially perpendicular angle. It should also be understood that, as with needles (600, 700) described above, facilitating tangential/oblique exit of suture (860) in both directions (e.g., away from tip (810) and away from tip (820)) may further facilitate passage of needle (800) through tissue in either direction (e.g., leading with tip (810) or leading with tip (820)). Needle (800) may thus be readily passed from arm (42) to arm (44) through tissue, then from arm (44) to arm (42) through tissue again.

F. Exemplary Needle with Sliding Suture Ball Joint

FIGS. 24-25 depict an exemplary needle (900) that includes an opposing pair of sharp tips (910, 920), and a central recess (930). While not shown, it should be understood that needle (900) may also include one or more features to facilitate grasping of needle (900). By way of example only, such features may be configured similar to grasping regions (540, 550) shown in FIGS. 14 and 16. As with any other sharp tip referred to herein, sharp tips (910, 920) may be configured in accordance with the above teachings relating to tip (110) and/or in any other suitable fashion. Central recess (930) may be formed using any suitable processes, including but not limited to MIM, folding around a die, milling, etc. Central recess (930) is configured to receive a ball (950) at the end of a suture (960). Ball (950) of the present example is fixedly secured to the end of suture (960). For instance, ball (950) may be crimped about the end of suture (960), may be adhered to suture (960), may be overmolded about suture (960), and/or may be secured to suture (960) in any other suitable fashion. Ball (950) may be formed of any suitable material, including but not limited to metal, plastic, etc. Ball (950) may also be formed through various kinds of microfabrication processes and/or other types of processes. By way of example only, ball (950) and/or at least a portion of suture (960) may be formed in accordance with at least some of the teachings of U.S. Pub. No. 2011/0054522, issued as U.S. Pat. No. 9,011,487 Apr. 21, 2015, the disclosure of which is incorporated by reference herein; and/or U.S. Pub. No. 2008/0161850, now abandoned, the disclosure of which is incorporated by reference herein. As another merely illustrative example, ball (950) may be formed as a melted knot at the end of suture (960). It should thus be understood that ball (950) and suture (960) of this example are substantially identical to ball (850) and suture (860) described above.

Needle (900) of this example is also substantially similar to needle (800) described above. However, rather than having features like localized crimps (832) that substantially maintain the position of ball (850) along the length of needle (800), needle (900) has crimps (932) that enable ball (950) to slide along a portion of the length of needle (800). Crimps (932) are formed adjacent to recess (930) and permit ball (950) to rotate and pivot relative to needle (900), in addition to allowing ball (950) to slide along part of the length of needle (900). It should be understood that ball (960) (and, hence, suture (960)) may rotate about various axes relative to needle (900), including axes that are perpendicular to the curvature of needle (900), axes that are tangent to the curvature of needle (900), and various axes in between such perpendicular and tangent axes. Crimps (932) nevertheless prevent ball (950) from falling out or being pulled out from recess (930). Crimps (932) also define an elongate slot (934) to provide further clearance for suture (960) as suture (960) and ball (950) are pivoted to positions where suture (960) is oriented substantially tangential or obliquely relative to needle (900). As noted above, providing a substantially non-perpendicular angle of exit for suture (960) relative to needle (900) may result in reduced drag forces and/or reduced tissue trauma as compared to a configuration where suture (960) exits needle (900) at a substantially perpendicular angle. It should also be understood that, as with needles (600, 700, 800) described above, facilitating tangential/oblique exit of suture (960) in both directions (e.g., away from tip (910) and away from tip (920)) may further facilitate passage of needle (900) through tissue in either direction (e.g., leading with tip (910) or leading with tip (920)). Needle (900) may thus be readily passed from arm (42) to arm (44) through tissue, then from arm (44) to arm (42) through tissue again. It should also be understood that the rotatability of ball (960) and suture (960) relative to needle (900) (e.g., about an axis perpendicular to the curvature of needle (900), about an axis tangent to the curvature of needle (900), etc.) may substantially prevent suture (960) from becoming undesirably wound up and/or tangled, etc., during a suturing procedure.

G. Exemplary Needle with Pivoting Suture Pin Joint

Figure 26:
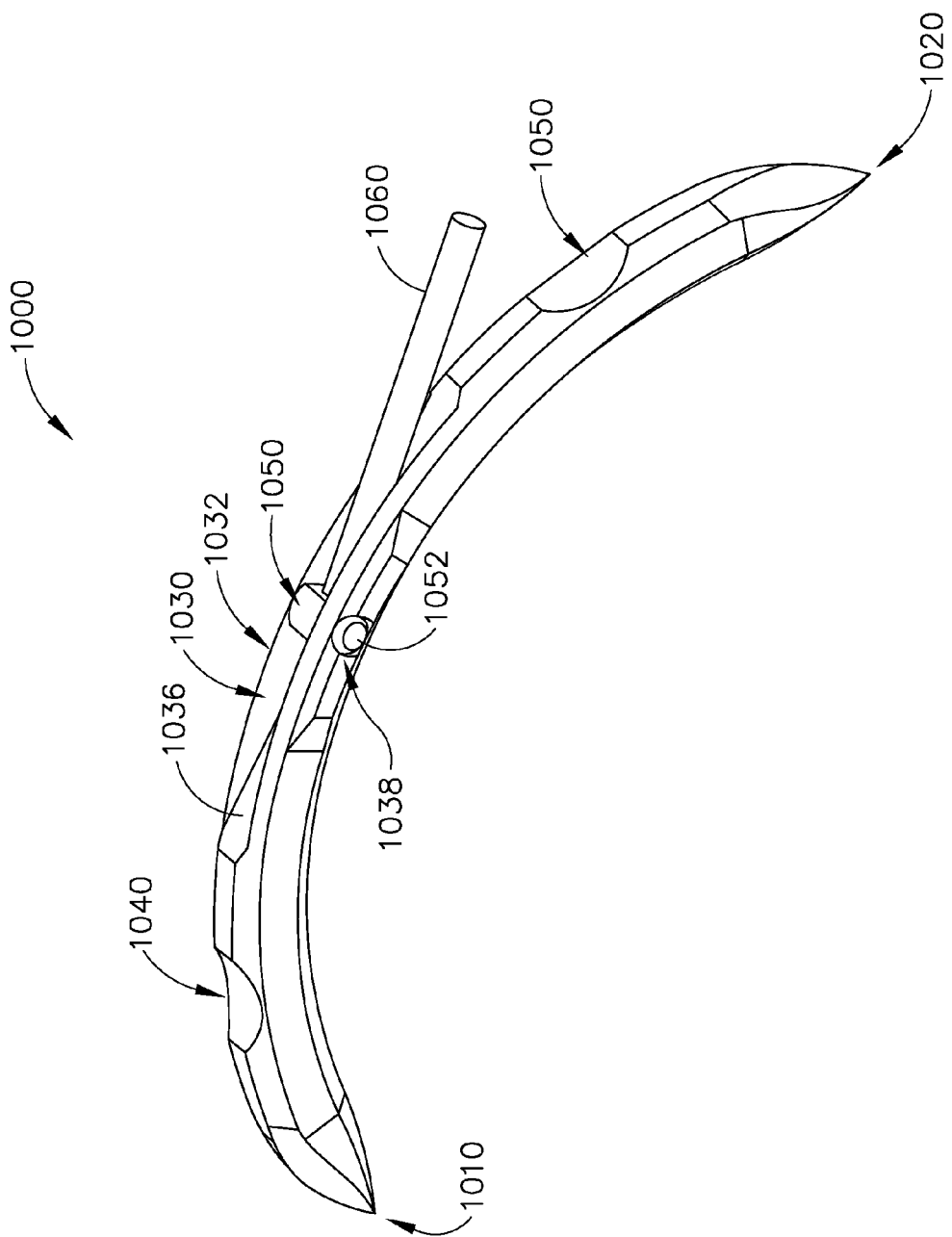
FIG. 26 depicts a perspective view of another exemplary alternative suturing needle.
Figure 27:
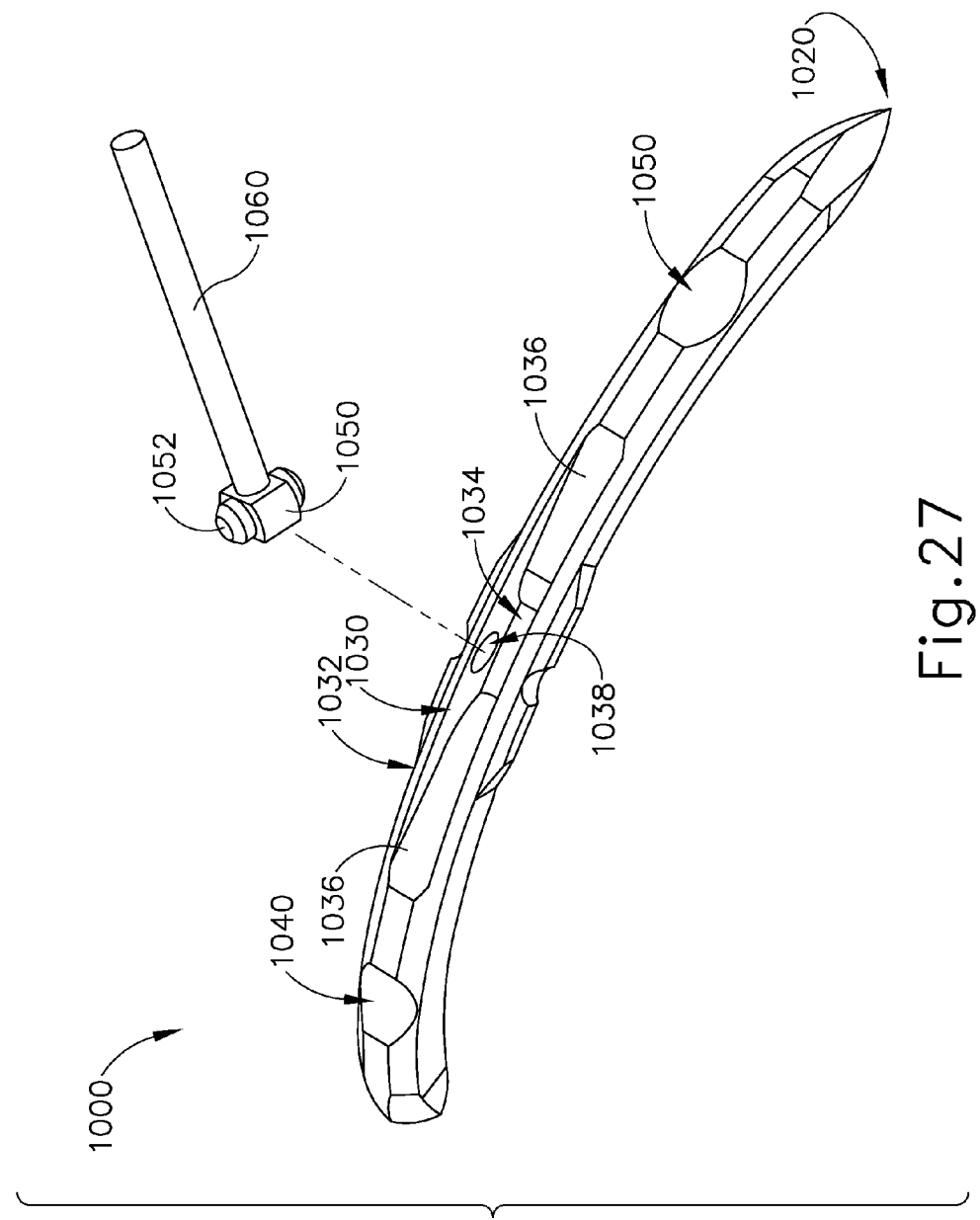
FIG. 27 depicts an exploded view of a suture separated from the needle of FIG. 26.

FIGS. 26-27 depict an exemplary needle (1000) that includes an opposing pair of sharp tips (1010, 1020), a central recess (1030), and a pair of grasping regions (1040, 1050). Sharp tips (1010, 1020) may be configured in accordance with the above teachings relating to tip (110) and/or in any other suitable fashion. Grasping regions (1040, 1050) may be configured in accordance with the above teachings relating to grasping regions (140, 150) and/or in any other suitable fashion. An upper opening (1032) and a lower opening (1034) communicate with central recess (1030). A pair of ramped surfaces (1036) extend between the outer ends of openings (1032, 1034). A pair of transverse openings (1038) are also in communication with central recess (1030). Transverse openings (1038) are aligned with each other and are configured to receive pins (1052) of a suture block (1050).

Suture block (1050) is fixedly secured to the end of a suture (1060). For instance, block (1050) may be crimped about the end of suture (1060), may be adhered to suture (1060), may be overmolded about suture (1060), and/or may be secured to suture (1060) in any other suitable fashion. Block (1050) may be formed of any suitable material, including but not limited to metal, plastic, etc. Block (1050) may also be formed through various kinds of microfabrication processes and/or other types of processes. By way of example only, block (1050) and/or at least a portion of suture (1060) may be formed in accordance with at least some of the teachings of U.S. Pub. No. 2011/0054522, issued as U.S. Pat. No. 9,011,487 on Apr. 21, 2015, the disclosure of which is incorporated by reference herein; and/or U.S. Pub. No. 2008/0161850, now abandoned, the disclosure of which is incorporated by reference herein. As another merely illustrative example, block (1050) may be formed as a melted knot at the end of suture (1060).

Pins (1052) may be formed as unitary features of block (1050). Alternatively, pins (1052) may comprise one or more components that are secured to block (1050) using any suitable techniques. The relationship between pins (1052) and transverse openings (1038) permits block (1050) and suture (1060) to rotate about the axis defined by pins (1052). The configuration of ramped surfaces (1036) and upper opening (1030) provide clearance for suture (1060) as suture (1060) and block (1050) are pivoted to positions where suture (1060) is oriented substantially tangential or obliquely relative to needle (1000). As noted above, providing a substantially non-perpendicular angle of exit for suture (1060) relative to needle (1000) may result in reduced drag forces and/or reduced tissue trauma as compared to a configuration where suture (1060) exits needle (1000) at a substantially perpendicular angle. It should also be understood that, as with needles (600, 700, 800, 900) described above, facilitating tangential/oblique exit of suture (1060) in both directions (e.g., away from tip (1010) and away from tip (1020)) may further facilitate passage of needle (1000) through tissue in either direction (e.g., leading with tip (1010) or leading with tip (1020)). Needle (1000) may thus be readily passed from arm (42) to arm (44) through tissue, then from arm (44) to arm (42) through tissue again.

Figure 28:
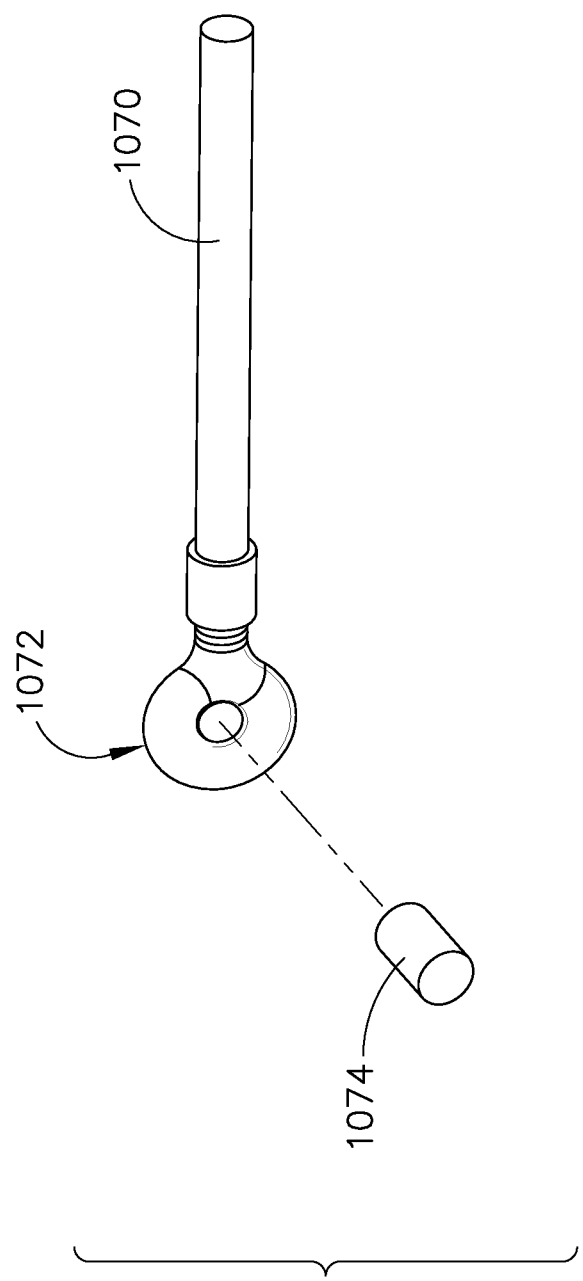
FIG. 28 depicts an exploded view of an exemplary alternative suture and pin for use with the needle of FIG. 26.

FIG. 28 depicts an exemplary alternative suture (1070) that may be used with needle (1000). Suture (1070) of this example includes an end loop (1072). End loop (1070) may be formed by suture (1070) or may be formed by a separate component that is secured to the end of suture (1070). Various suitable ways in which end loop (1072) may be provided will be apparent to those of ordinary skill in the art in view of the teachings herein. A pin (1074) is inserted through end loop (1072) and is also configured to fit in transverse openings (1038) of needle (1000). Suture (1070) and end loop (1072) are operable to rotate about the axis defined by pin (1074). Thus, end loop (1072) and pin (1074) together provide functionality similar to that provided by block (1050) and pins (1052) described above. In some versions, pin (1074) rotates with end loop (1072) and suture (1070), relative to needle (1000). In some other versions, pin (1074) is substantially fixed relative to needle (1000), and end loop (1072) rotates with suture (1070) relative to pin (1074) and relative to needle (1000). Still other suitable components, features, configurations, and operabilities will be apparent to those of ordinary skill in the art in view of the teachings herein.

H. Exemplary Needle with Double Leg Suture

FIGS. 29-30 depict an exemplary needle (1100) and that includes an opposing pair of sharp tips (1110, 1120), and a central recess (1130). While not shown, it should be understood that needle (1100) may also include one or more features to facilitate grasping of needle (1100). By way of example only, such features may be configured similar to grasping regions (540, 550) shown in FIGS. 14 and 16. As with any other sharp tip referred to herein, sharp tips (1110, 1120) may be configured in accordance with the above teachings relating to tip (110) and/or in any other suitable fashion. Central recess (1130) may be formed using any suitable processes, including but not limited to MIM, folding around a die, milling, etc. Central recess (1130) is configured to receive a collar (1150) in the middle of a suture (1160). Collar (1150) of the present example is fixedly secured to suture (1160), and facilitates attachment of suture (1160) to needle (1100). By way of example only, collar (1150) may be crimped about suture (1160), may be adhered to suture (1160), may be overmolded about suture (1160), and/or may be secured to suture (1160) in any other suitable fashion. Collar (1150) may be formed of any suitable material, including but not limited to metal, plastic, etc. As another merely illustrative example, collar (1150) may be formed as a melted knot in suture (1160). In the present example, suture (1160) extends to equal lengths from each end of collar (1150), such that suture (1160) is provided as a double leg suture. Of course, in some versions suture (1160) may extend only from one end of collar (1150). Furthermore, in versions where suture (1160) extends from both ends of collar (1150), a surgeon may simply cut off one leg of suture (1160) at any appropriate time, as desired.

Needle (1100) retains collar (1150) in this example with localized crimps (1132) formed adjacent to central recess (1130). The relationship between collar (1150) and needle (1100) may nevertheless enable collar (1150) to rotate within central recess (1130), about the longitudinal axis defined by collar (1150). Thus, suture (1160) may rotate relative to needle (1100), about the central axis defined by collar (1150), which is oriented generally tangentially or obliquely relative to needle (1100). Such rotatability of suture (1160) may substantially prevent suture (1160) from becoming undesirably wound up and/or tangled, etc., during a suturing procedure. A pair of opposing elongate slots (1134) adjacent to crimps (1132) provide further clearance for suture (1160) to enable suture (1160) to be oriented substantially tangential or obliquely relative to needle (1100). As noted above, providing a substantially non-perpendicular angle of exit for suture (1160) relative to needle (1100) may result in reduced drag forces and/or reduced tissue trauma as compared to a configuration where suture (1160) exits needle (1100) at a substantially perpendicular angle. It should also be understood that, as with needles (600, 700, 800, 900, 1000) described above, facilitating tangential/oblique exit of suture (1160) in both directions (e.g., away from tip (1110) and away from tip (1120)) may further facilitate passage of needle (1100) through tissue in either direction (e.g., leading with tip (1110) or leading with tip (1120)). Needle (1100) may thus be readily passed from arm (42) to arm (44) through tissue, then from arm (44) to arm (42) through tissue again. In some versions, the central axis of collar (1150) runs along or tangent to a portion of the center line of needle (1100).

I. Exemplary Needle with Suture Retention Plate

Figure 31:
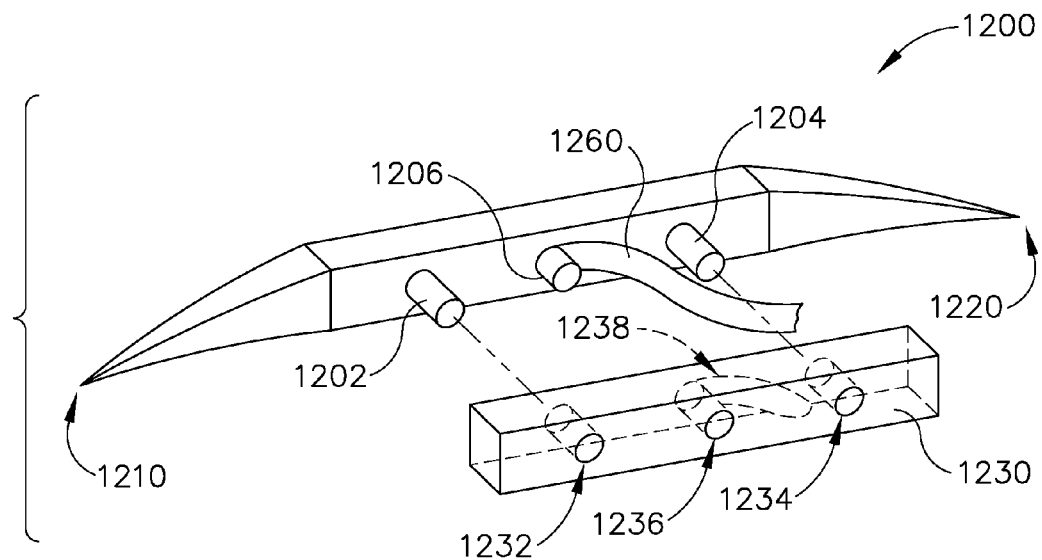
FIG. 31 depicts an exploded perspective view of another exemplary alternative suturing needle.

FIG. 31 depicts an exemplary needle (1200) that includes an opposing pair of sharp tips (1210, 1220), and a retention plate (1230). While not shown, it should be understood that needle (1200) may also include one or more features to facilitate grasping of needle (1200). By way of example only, such features may be configured similar to grasping regions (540, 550) shown in FIGS. 14 and 16. As with any other sharp tip referred to herein, sharp tips (1210, 1220) may be configured in accordance with the above teachings relating to tip (110) and/or in any other suitable fashion. A pair of guide posts (1202, 1204) and a suture post (1206) extend transversely from needle (1200). Retention plate (1230), as a pair of openings (1232, 1234) that correspond with guide posts (1202, 1204), respectively; and an opening (1236) that corresponds with suture post (1206). In the present example, guide posts (1202, 1204) and openings (1232, 1234) are dimensioned to provide an interference fit, such that retention plate (1230) may be secured to needle (1200) through friction. Of course, any other suitable features or techniques may be used to secure retention plate (1230) to needle (1200), including but not limited to welding, adhesives, etc. It should also be understood that, to the extent that any guide posts (1202, 1204) are used at all, more or less than two guide posts (1202, 1204) may be used.

In the present example, a suture (1260) is wrapped about suture post (1206). With suture (1260) positioned about suture post (1206), with suture post (1206) disposed in opening (1236), and with retention plate (1230) secured to needle (1200), suture (1260) is thereby secured to needle (1200). In some versions, suture post (1206) and opening (1236) are dimensioned to provide an interference fit. In some other versions, suture post (1206) and opening (1236) are omitted. For instance, suture (1260) may simply be captured between needle (1200) and retention plate (1230), and the resulting friction on suture (1260) may suffice to secure suture (1260) to needle (1200). Various other suitable ways in which suture (1260) may be secured to needle (1200) will be apparent to those of ordinary skill in the art in view of the teachings herein. Retention plate (1230)

includes a guide channel (1238) configured to receive and guide suture (1260). Guide channel (1238) is formed on the side of retention plate (1230) that faces needle (1200). Guide channel (1238) is oriented to provide an angle of exit for suture (1260) that is substantially tangent or oblique relative to needle (1200). As noted above, providing a substantially non-perpendicular angle of exit for suture (1260) relative to needle (1200) may result in reduced drag forces and/or reduced tissue trauma as compared to a configuration where suture (1260) exits needle (1200) at a substantially perpendicular angle.

J. Exemplary Needle with Resilient Suture Retainer

Figure 32:
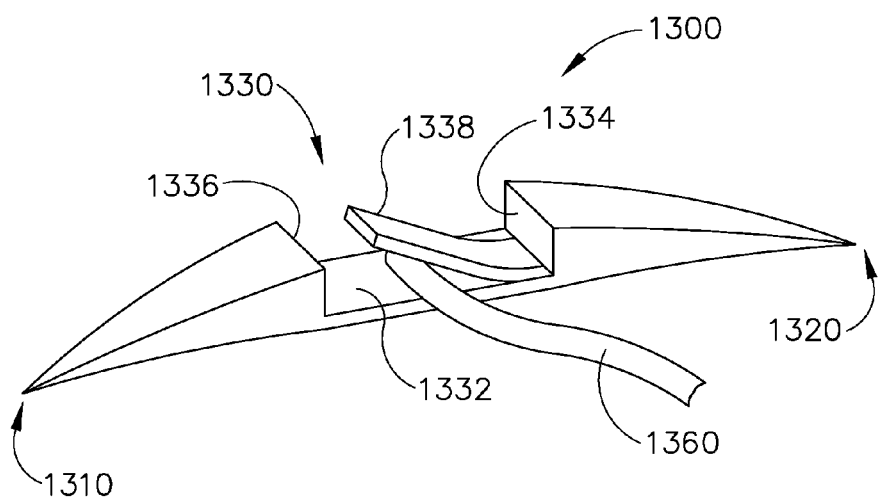
FIG. 32 depicts a perspective view of another exemplary suturing needle.

FIG. 32 depicts an exemplary needle (1300) that includes an opposing pair of sharp tips (1310, 1320), and a central recess (1330). While not shown, it should be understood that needle (1300) may also include one or more features to facilitate grasping of needle (1300). By way of example only, such features may be configured similar to grasping regions (540, 550) shown in FIGS. 14 and 16. As with any other sharp tip referred to herein, sharp tips (1310, 1320) may be configured in accordance with the above teachings relating to tip (110) and/or in any other suitable fashion. Central recess (1330) is defined by a floor (1332) and a pair of opposing endwalls (1334, 1336). A resilient tab (1336) extends at an angle from the intersection of endwall (1334) and floor (1332). Tab (1336) is resiliently biased toward floor (1332). A suture (1360) is captured between tab (1336) and floor (1332). The resilient bias of tab (1336) against suture (1360) is sufficient to secure suture (1360) to needle (1300). In some other versions, tab (1336) is malleable, and is bent over suture to secure suture (1360) to needle (1300). In the present example, suture (1360) is captured under tab (1336) at an angle such that the exit of suture (1360) is oriented substantially tangent or oblique relative to needle (1300). As noted above, providing a substantially non-perpendicular angle of exit for suture (1360) relative to needle (1300) may result in reduced drag forces and/or reduced tissue trauma as compared to a configuration where suture (1360) exits needle (1300) at a substantially perpendicular angle. In some versions, endwalls (1334) are formed at an angle to further promote oblique exit of suture (1360).

III. Miscellaneous

In any of the examples

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
(a) a surgical needle, wherein the surgical needle comprises:
(i) a first end, wherein the first end includes a first sharp point configured to pierce tissue,
(ii) a second end, and
(iii) a mid-region extending between the first end and the second end, wherein the mid-region defines a transverse opening;
(b) a suture, wherein the suture comprises:
(i) a first end, and
(ii) a second end; and
(c) a coupling member secured to the second end of the suture, wherein the coupling member is further secured to the mid-region of the surgical needle, wherein the coupling member is configured to rotate relative to the surgical needle, wherein the coupling member comprises a pin and a coupling body, wherein the pin is located within the transverse opening, wherein the coupling body is connected to the pin, wherein the second end of the suture is fixed to the coupling body.

2. The apparatus of claim 1, wherein the coupling member is configured to rotate about an axis that is perpendicular to a line extending from the first end of the needle to the second end of the needle through the mid-region.

3. The apparatus of claim 1, wherein the surgical needle further comprises a substantially flat side surface extending along at least part of the length of the mid-region.

4. The apparatus of claim 1, wherein the mid-region includes at least one area of increased thickness.

5. The apparatus of claim 1, wherein the first sharp point includes three converging cutting edges, at least two planer surfaces bounded by three cutting edges, and a rounded surface bounded by two of the three cutting edges.

6. The apparatus of claim 1, wherein the coupling body comprises a suture block.

7. The apparatus of claim 6, wherein the suture block is free to pivot relative to the pin.

8. The apparatus of claim 6, wherein the suture block is fixed to the pin.

9. The apparatus of claim 1, wherein the mid-region defines a central recess, wherein the pin is located within a space defined by the central recess.

10. The apparatus of claim 9, wherein the mid-region defines an opening configured to provide access to the central recess.

11. The apparatus of claim 9, wherein the mid-region further comprises a first ramped surface, wherein the first ramped surface declines towards the pin.

12. the apparatus of claim 11, wherein the first ramped surface extends from an upper opening to a lower opening.

13. The apparatus of claim 1, wherein the surgical needle comprises at least one feature configured for grasping by a suturing instrument.

14. The apparatus of claim 13, wherein the at least one feature configured for grasping by a suturing instrument comprises a notch formed in an exterior surface of the surgical needle.

15. The apparatus of claim 14, wherein the surgical needle is curved along a plane of curvature, wherein the notch comprises a scallop formed along a plane of curvature.

16. An apparatus, comprising:
 (a) a surgical needle, wherein the surgical needle comprises:
  (i) a first end, wherein the first end includes a first sharp point configured to pierce tissue,
  (ii) a second end, and
  (iii) a mid-region extending between the first end and the second end,
   wherein the mid-region comprises:
   (A) a first side wall defining an opening,
   (B) a second side wall parallel with the first side wall,
   (B) a pair of ramped surfaces at least partially defined by the first side wall and the second side wall, wherein the first side wall, the second side wall, and the pair of ramped surfaces define a recess; and
 (b) a suture, wherein the suture comprises:
  (i) a first end, and
  (ii) a second end; and
 (c) a coupling member secured to the second end of the suture, wherein the coupling member comprises a pin and a coupling body, wherein the pin is at least partially housed within the opening of the first side wall, wherein the coupling body is housed within the recess between the first side wall and the second side wall.

17. The apparatus of claim 16, wherein the pair of ramped surfaces are inclined at opposing angles.

18. The apparatus of claim 17, wherein the suture is configured to rotate with the coupling member to contact one ramped surface of the pair of ramped surfaces.

19. An apparatus, comprising:
 (a) a surgical needle, wherein the surgical needle comprises:
  (i) a first end, wherein the first end includes a first sharp point configured to pierce tissue,
  (ii) a second end, wherein the second end includes a second sharp point configured to pierce tissue, and
  (iii) a mid-region extending between the first end and the second end;
 (b) a suture, wherein the suture comprises:
  (i) a first end, and
  (ii) a second end; and
 (c) a coupling member comprising:
  (i) a pin pivotally coupled to the mid-region, and
  (ii) a suture block associated with the pin, wherein the suture block is secured to the second end of the suture.

\* \* \* \* \*